(12) United States Patent
Stewart et al.

(10) Patent No.: US 7,083,976 B2
(45) Date of Patent: Aug. 1, 2006

(54) TYROSINE RECOMBINASE FOR GENETIC ENGINEERING

(75) Inventors: A. Francis Stewart, Leimen (DE); Youming Zhang, Heidelberg (DE); Bernard Hallet, Sombreffe (BE)

(73) Assignees: The European Molecular Biology Laboratory, Heidelberg (DE); l 'Universite catholique de Louvain, Louvain-la Neuve (BE)

( * ) Notice: Subject to any disclaimer, the term of this patent is extended or adjusted under 35 U.S.C. 154(b) by 88 days.

(21) Appl. No.: 09/895,435

(22) Filed: Jun. 30, 2001

(65) Prior Publication Data

US 2003/0113837 A1    Jun. 19, 2003

(51) Int. Cl.
*C07H 21/04*    (2006.01)
*C12N 15/00*    (2006.01)

(52) U.S. Cl. .................. 435/325; 435/6; 435/252.3; 435/320.1; 536/23.1; 536/23.2

(58) Field of Classification Search .............. 435/6, 435/325, 252.3, 320.1; 536/23.1, 23.2; 530/350, 530/300
See application file for complete search history.

(56) References Cited

FOREIGN PATENT DOCUMENTS

WO       WO 01/04288 A1    1/2001

OTHER PUBLICATIONS

Buchholz et al., 1996, "Different thermostabilities of FDP and Cre recombinases: implications for applied site-specific recombination", Nucl. Acids Res. 24:256-262.
Kilby et al., 1993, "Site-specific recombinases: tools for genome engineering", Trends Genet. 9:413-421.
Logie and Stewart, 1995, "Ligand-regulated site-specific recombination", Proc. Natl.Acad. Sci. USA 92:5940-5944.
Mahillon and Lececlus, 1988, "Structural and functional analysis of Tn4430: identification of an integrase-like protein involved in the co-integrate-resolution process", EMBO J. 7:1515-1526.
Metzger and Feil, 1999, "Engineering the mouse genome by site-specific recombination", Current Opin. Biotechnol. 10:470-476.
Meyers et al., 1998, "Am Fgf8 mutant allelic series generated by Cre- and Flp-mediated recombination", Nature Genetics 18:136-141.
Ringrose et al., 1998, "Comparative kinetic analysis of FLP and cre recombinases: mathematical models for DNA binding and recombination", J. Mol. Biol. 284:363-384.
Salamitou et al., 1997, "A genetic system that reports transient activation of genes in Bacillus", Gene 202:121-126.
Sanchis et al., 1997, "A recombinase-mediated system for elimination of antibiotic resistance gene markers from genetically engineered *Baccillus thuringiensis* strains", Appl. Environ. Microbiol. 63:779-784.
Sauer, 1998, "Inducible gene targeting in mice using the Cre/lox system", Methods 14:381-392.
Mahillon J. et al, "Complete Nucleotide Sequence of PGI-2 A Bacillus-Thuringiensis Plasmid Containing TN-4430"; Nucleic Acids Research, vol. 16, No. 24, 1988, pp. 11827-11828.
Mahillon J et al., "IS231 and other *Bacillus thuringiensis* transposable elements: A review"; Genetica (Dordrecht), vol. 93, No. 1-3, 1994, pp. 13-26.
NG P et al, "A High-Effiency CRE/LOXP-Based System For Construction Of Adenoviral Vectors"; Human Gene Therapy, XX, XX, vol. 10, No. 16, Nov. 1, 1999, pp. 2667-2672.
Ringrose Leonie et al., "The Kw recombinase, an integrase from *Kluyveromyces waltii*"; European Journal of Biochemistry, vol. 248, No. 3, 1997, pp. 903-912.

*Primary Examiner*—Sean McGarry
(74) *Attorney, Agent, or Firm*—Amster, Rothstein & Ebenstein LLP

(57) ABSTRACT

The present invention is directed to methods and compositions for TnpI-mediated genetic engineering using the *Bacillus thuringiensis* recombinase TnpI and the TnpI recombination substrates TRT or TRT', and variants thereof. In particular, the invention relates to TRT or TRT' sequences, and variants thereof, vectors, cells and kits useful for TnpI-mediated genetic recombination, as well as methods for the use of TRT or TRT' sequences for TnpI-mediated genetic engineering.

35 Claims, 13 Drawing Sheets

Tnp1 recognized target (TRT)

Figure 2:
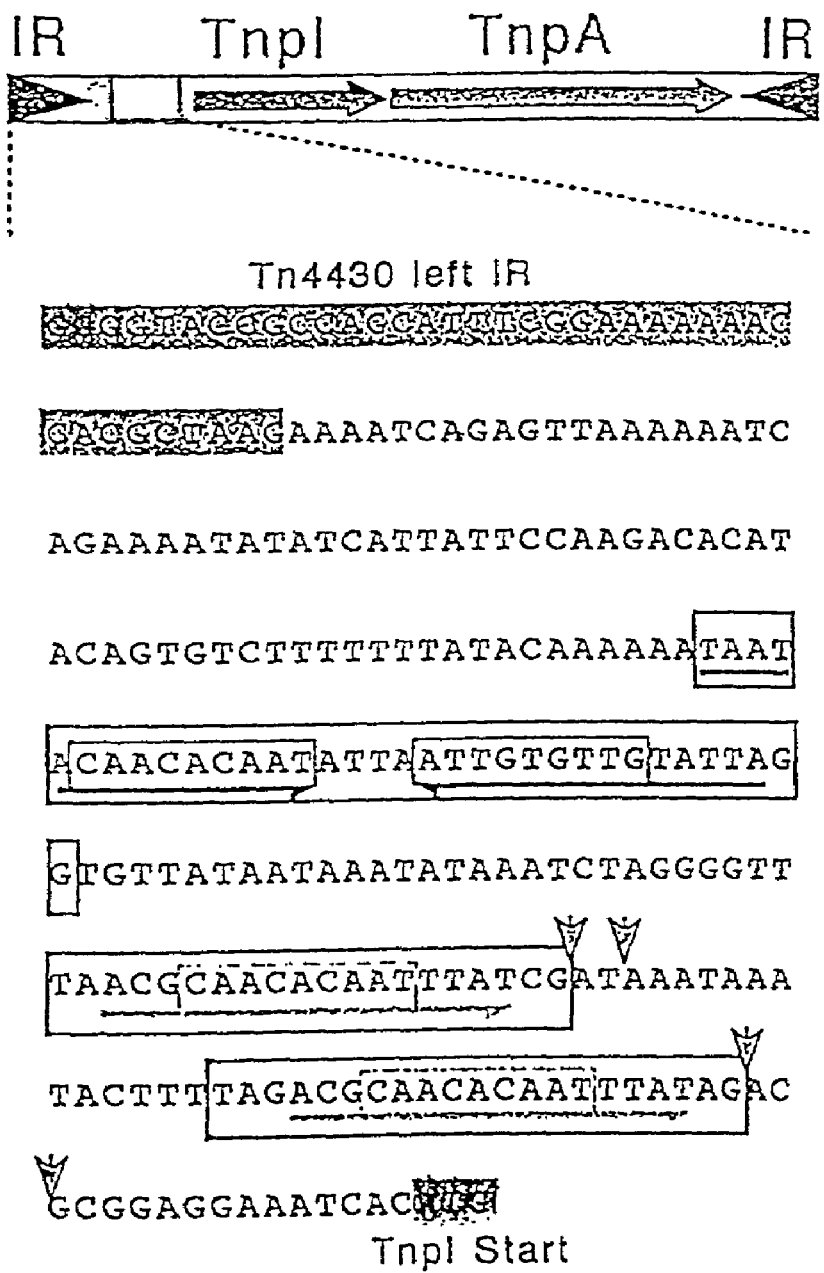

A  TRT" (244bp)
*GGTACCGCCAGCATTTCGGAAAAAAACCACGCTAAG<u>AAAATCAGA</u>GTTA<u>AAA*</u>

<u>*AATCAGA*</u>*AAATATATCATTATTCCAAGACACATACAGTGTCTTTTTTTATACAA*

*AAAA<u>TAATACAACACAAT</u>ATTA<u>ATTGTGTTGTATTA</u>GGTGTTATAATA*

*AATATAAATCTAGGGGTTTA<u>ACGCAACACAATTTAT</u>CGATAAATAAAT*

*ACTTTTAG<u>ACGCAACACAATTTAT</u>AGACGCGGAGGAAATCAC*

B  TRT' (116bp)
<u>TAATACAACACAAT</u>ATTA<u>ATTGTGTTGTATTA</u>GGTGTTATAATAAATA

TAAATCTAGGGGTTTA<u>ACGCAACACAATTTAT</u>CGATAAATAAATACTTT

TAG<u>ACGCAACACAATTTAT</u>AGACGCGGAGGAAATCAC

C  TRT (32bp)
<u>TAATACAACACAAT</u>ATTA<u>ATTGTGTTGTATTA</u>

FIG. 1A-C

```
  1 ATG GAT GTT GCA AAA CAG TTT TCT TCT TAT CTT AAA CAA GAG AAT AAA ACC GAG AAC
  1>Met Asp Val Ala Lys Gln Phe Ser Ser Tyr Leu Lys Gln Glu Asn Lys Thr Glu Asn

58 ACT GTT CAG GGA TAC ACA TCA GGT ATT AGA CAG TAC ATA AAA TGG TTT GAA GGT TCC
 20>Thr Val Gln Gly Tyr Thr Ser Gly Ile Arg Gln Tyr Ile Lys Trp Phe Glu Gly Ser

115 TAT GAC AGA AAA TTA ACA AAA TTG TAC CGA CAA AAT ATC TTA GAG TAC ATT AGT TAT
 39>Tyr Asp Arg Lys Leu Thr Lys Leu Tyr Arg Gln Asn Ile Leu Glu Tyr Ile Ser Tyr

172 TTA AAG AAT GTC AAA ATG TTG AAC GCC AAG TCC ATT AAC CAC AAG ATT AGT AGC CTT
 58>Leu Lys Asn Val Lys Met Leu Asn Ala Lys Ser Ile Asn His Lys Ile Ser Ser Leu

229 GCT AAA TTT AAT GAA TTT CTA ATA CAG AAA GGA AGT CAA CAA GAT CAA GTA ATT TTA
 77>Ala Lys Phe Asn Glu Phe Leu Ile Gln Lys Gly Ser Gln Gln Asp Gln Val Ile Leu

286 AAA ACA GAC ATG ATA AAG GTT CAA ACT GTC TAT GCT TCT CCA ACC CAA ATT GTT GAA
 96>Lys Thr Asp Met Ile Lys Val Gln Thr Val Tyr Ala Ser Pro Thr Gln Ile Val Glu

343 TTA GAT GTA AAA AAG TTT TTA CAA AGT GTG TTA GAG GAT AAT AAC AAA CGT AAT TAT
115>Leu Asp Val Lys Cys Phe Leu Gln Ser Val Leu Glu Asp Asn Asn Lys Arg Asn Tyr

400 GCA ATT GCC ACT CTC CTA GCA TAT ACA GGA GTA CGT ATT TCA GAG GCA TTA TCT ATC
134>Ala Ile Ala Thr Leu Leu Ala Tyr Thr Gly Val Arg Ile Ser Glu Ala Leu Ser Ile

457 AAA ATG AAT GAC TTC AAT TTA CAG ACT GGG GAA TGT ATT ATT CGA AGT GGA AAA GGA
153>Lys Met Asn Asp Phe Asn Leu Gln Thr Gly Glu Cys Ile Ile Arg Ser Gly Lys Gly

514 GGT AAA CAA CGA ATT GTA TTA CTA AAT AGT AAG GTA CTT AGT GCT ATC AAA GAT TAT
172>Gly Lys Gln Arg Ile Val Leu Leu Asn Ser Lys Val Leu Ser Ala Ile Lys Asp Tyr

571 CTC ATC GAT CGA AAA ACA TAC AGT ACA GCA CAT GAA TCT CCG TAT CTT TTT ATT AGT
191>Leu Ile Asp Arg Lys Thr Tyr Ser Thr Ala His Glu Ser Pro Tyr Leu Phe Ile Ser

628 AAA AAG CGA GAA AAG CTC GAC CGT ACG GTC GTC AAT CGT ATC TTT AAA TCA TAC AGC
210>Lys Lys Arg Glu Lys Leu Asp Arg Thr Val Val Asn Arg Ile Phe Lys Ser Tyr Ser

685 AAT GTT ATT ACT CCA CAC CAA TTA CGA CAC TTC TTC TGT ACG AAT GCA ATT GAA AAA
229>Asn Val Ile Thr Pro His Gln Leu Arg His Phe Phe Cys Thr Asn Ala Ile Glu Lys

742 GGA TTT AGC ATT CAT GAA GTT GCA AAT CAA GCT GGG CAC TCT AAC ATC CAT ACG ACA
248>Gly Phe Ser Ile His Glu Val Ala Asn Gln Ala Gly His Ser Asn Ile His Thr Thr

799 CTA CTT TAC ACA AAT CCA AAC CAA CTG CAG CTA AAA AAT AAA ATG GAG CTC TTA TAA
267>Leu Leu Tyr Thr Asn Pro Asn Gln Leu Gln Leu Lys Asn Lys Met Glu Leu Leu ***
```

FIG. 3

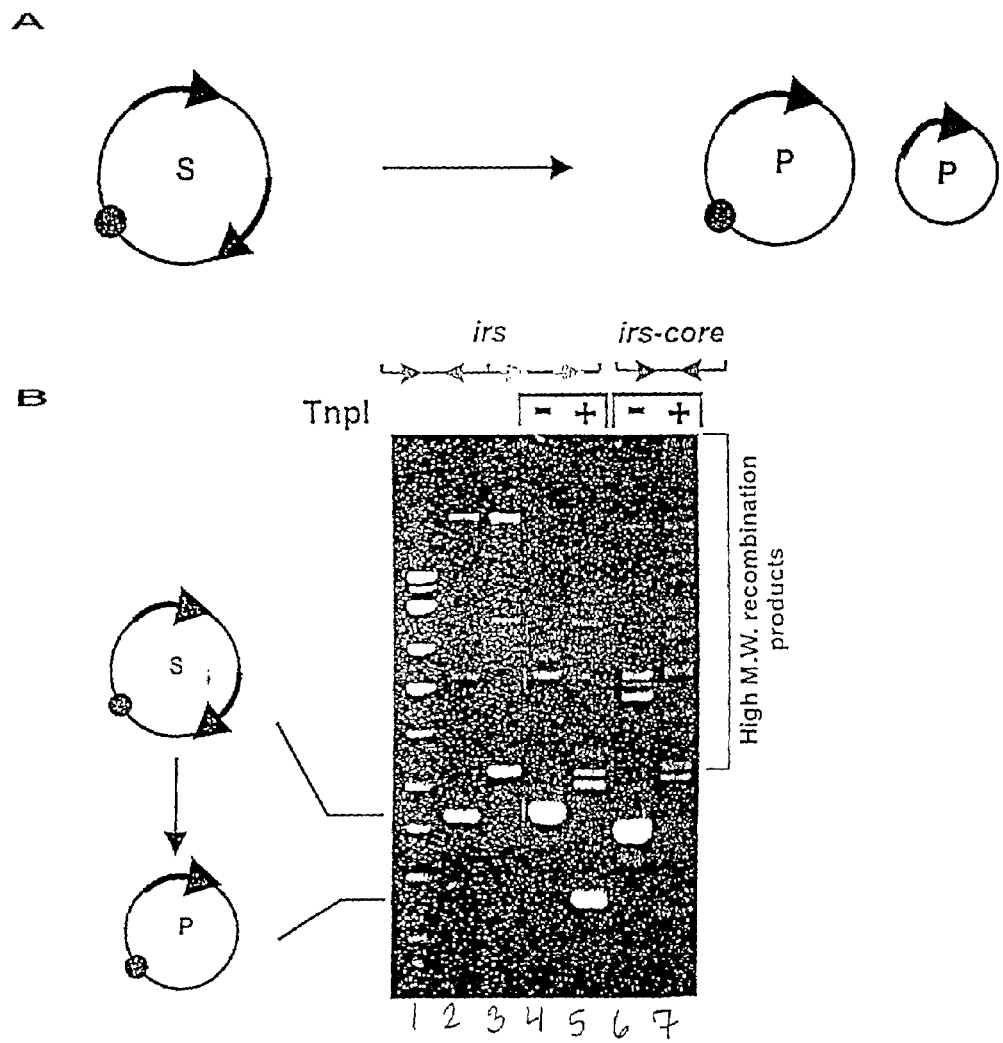
FIG. 5A-B

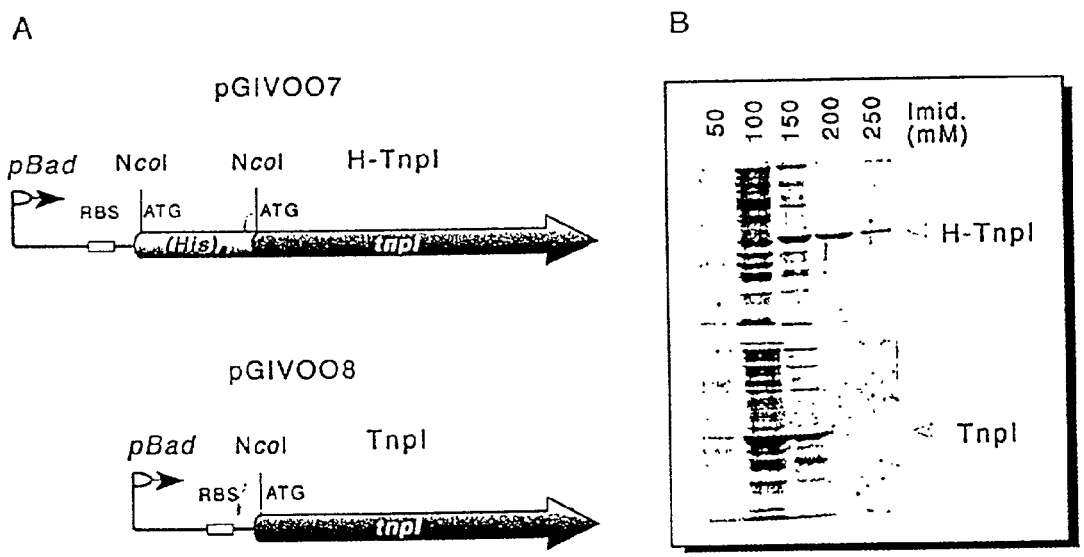
FIG. 6A-B

A
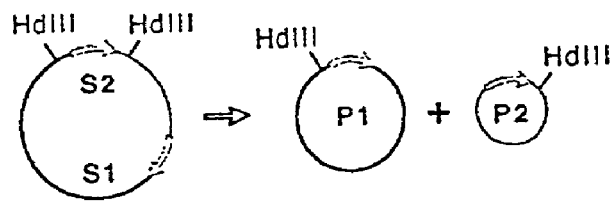
B
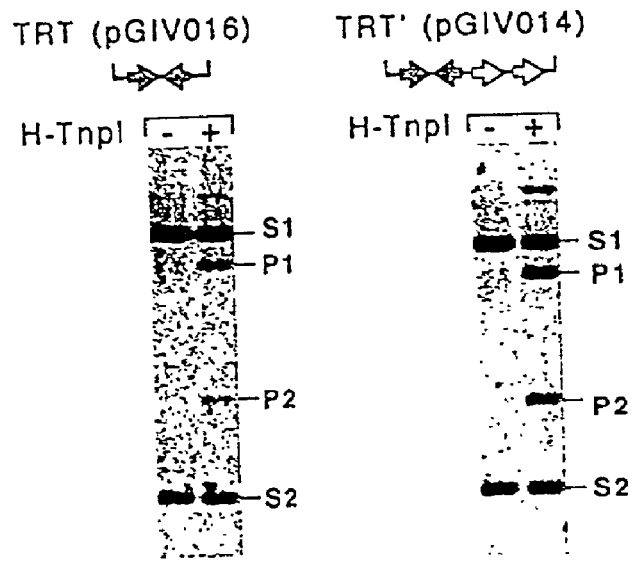
C
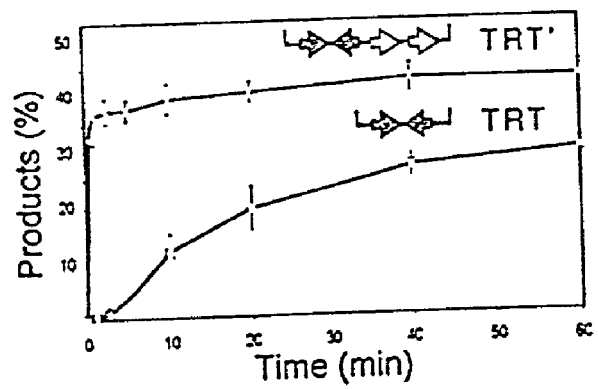
FIG. 7A-C

SEQUENCE LISTING

<160> NUMBER OF SEQ ID NOS: 10

<210> SEQ ID NO 1
<211> LENGTH: 244
<212> TYPE: DNA
<213> ORGANISM: Bacillus thuringiensis

<400> SEQUENCE: 1

| ggtaccgcca gcatttcgga aaaaaccac gctaagaaaa tcagagttaa aaaatcagaa | 60 |
| aatatatcat tattccttga cacatacatg ttcttttttt atacaaaaaa taatacaaca | 120 |
| caatattaat tgtgttgtat taggtgttat aataaatata aatctagggg tttaacgcaa | 180 |
| cacaattttat cgataaataa atacttttag acgcaacaca atttatagac gcggaggaaa | 240 |
| tcac | 244 |

<210> SEQ ID NO 2
<211> LENGTH: 118
<212> TYPE: DNA
<213> ORGANISM: Bacillus thuringiensis

<400> SEQUENCE: 2

| taatacaaca caatattaat tgtgttgtat taggtgttat aataaatata aatctagggg | 60 |
| tttaacgcaa cacaatttat cgataaataa atacttttag acgcaacaca atttatag | 118 |

<210> SEQ ID NO 3
<211> LENGTH: 32
<212> TYPE: DNA
<213> ORGANISM: Bacillus thuringiensis

<400> SEQUENCE: 3

| taatacaaca caatattaat tgtgttgtat ta | 32 |

<210> SEQ ID NO 4
<211> LENGTH: 249
<212> TYPE: DNA
<213> ORGANISM: Bacillus thuringiensis

<400> SEQUENCE: 4

| ggggtaccgc cagcatttcg gaaaaaaacc acgctaagaa aatcagagtt aaaaaatcag | 60 |
| aaaatatatc attattcctt gacacataca tgttctttttt ttatacaaaa aataatacaa | 120 |
| cacaatatta attgtgttgt attaggtgtt ataataaata taaatctagg ggtttaacgc | 180 |
| aacacaattt atcgataaat aaatactttt agacgcaaca caatttatag acgcggagga | 240 |
| aatcacatg | 249 |

<210> SEQ ID NO 5
<211> LENGTH: 798
<212> TYPE: DNA
<213> ORGANISM: Bacillus thuringiensis
<220> FEATURE:
<221> NAME/KEY: CDS
<222> LOCATION: (1)..(798)

<400> SEQUENCE: 5

| atg gat gtt gca aaa cag ttt tct tct tat ctt aaa caa gag aat aaa | 48 |
| Met Asp Val Ala Lys Gln Phe Ser Ser Tyr Leu Lys Gln Glu Asn Lys | |
| 1               5                   10                  15 | |

| acc gag aac act gtt cag gga tac aca tca ggt att aga cag tac ata | 96 |
| Thr Glu Asn Thr Val Gln Gly Tyr Thr Ser Gly Ile Arg Gln Tyr Ile | |

```
                      20                   25                   30
aaa tgg ttt gaa ggt tcc tat gac aga aaa ttg aca aaa ttg tac cga       144
Lys Trp Phe Glu Gly Ser Tyr Asp Arg Lys Leu Thr Lys Leu Tyr Arg
         35                   40                   45 caa aat atc tta gag tac att agt tat tta aag aat gtc aaa atg ttg       192
Gln Asn Ile Leu Glu Tyr Ile Ser Tyr Leu Lys Asn Val Lys Met Leu
 50                   55                   60 aac gcc aag tcc att aac cac aag att agt agc ctt gct aaa ttt aat       240
Asn Ala Lys Ser Ile Asn His Lys Ile Ser Ser Leu Ala Lys Phe Asn
 65                   70                   75                   80 gaa ttt cta ata cag aaa gga agt caa caa gat caa gta att tta tta       288
Glu Phe Leu Ile Gln Lys Gly Ser Gln Gln Asp Gln Val Ile Leu Leu
                 85                   90                   95 gat gta aaa aag ttt tta caa agt gtg tta gag gat aat aac aaa cgt       336
Asp Val Lys Lys Phe Leu Gln Ser Val Leu Glu Asp Asn Asn Lys Arg
            100                  105                  110 aat tat gca att gcc act ctc cta gca tat aca gga gta cgt att tca       384
Asn Tyr Ala Ile Ala Thr Leu Leu Ala Tyr Thr Gly Val Arg Ile Ser
        115                  120                  125 gag gca tta tct atc aaa atg aat gac ttc aat tta cag act ggg gaa       432
Glu Ala Leu Ser Ile Lys Met Asn Asp Phe Asn Leu Gln Thr Gly Glu
    130                  135                  140 tgt att att cga agt gga aaa gga ggt aaa caa cga att gta tta cta       480
Cys Ile Ile Arg Ser Gly Lys Gly Gly Lys Gln Arg Ile Val Leu Leu
145                  150                  155                  160 aat agt aag gta ctt agt gct atc aaa gat tat ctc atc gat cga aaa       528
Asn Ser Lys Val Leu Ser Ala Ile Lys Asp Tyr Leu Ile Asp Arg Lys
                 165                  170                  175 aca tac agt aca gca cat gaa tct ccg tat ctt ttt att agt aaa aag       576
Thr Tyr Ser Thr Ala His Glu Ser Pro Tyr Leu Phe Ile Ser Lys Lys
            180                  185                  190 cga gaa aag ctc gac cgt acg gtc gtc aat cgt atc ttt aaa tca tac       624
Arg Glu Lys Leu Asp Arg Thr Val Val Asn Arg Ile Phe Lys Ser Tyr
        195                  200                  205 agg aat gtt att act cca cac caa tta cga cac ttc ttc tgt acg aat       672
Arg Asn Val Ile Thr Pro His Gln Leu Arg His Phe Phe Cys Thr Asn
    210                  215                  220 gca att caa aaa gga ttt agc att cat gaa gtt gca aat caa gct ggg       720
Ala Ile Gln Lys Gly Phe Ser Ile His Glu Val Ala Asn Gln Ala Gly
225                  230                  235                  240 cac tct aac atc cat acg aca cta ctt tac aca aat cca aac caa ctg       768
His Ser Asn Ile His Thr Thr Leu Leu Tyr Thr Asn Pro Asn Gln Leu
                 245                  250                  255 cag cta aaa aat aaa atg gag ctc tta taa                               798
Gln Leu Lys Asn Lys Met Glu Leu Leu
            260                  265

<210> SEQ ID NO 6
<211> LENGTH: 265
<212> TYPE: PRT
<213> ORGANISM: Bacillus thuringiensis

<400> SEQUENCE: 6

Met Asp Val Ala Lys Gln Phe Ser Ser Tyr Leu Lys Gln Glu Asn Lys
 1               5                  10                   15

Thr Glu Asn Thr Val Gln Gly Tyr Thr Ser Gly Ile Arg Gln Tyr Ile
             20                   25                   30

Lys Trp Phe Glu Gly Ser Tyr Asp Arg Lys Leu Thr Lys Leu Tyr Arg
         35                   40                   45
```

-continued

```
Gln Asn Ile Leu Glu Tyr Ile Ser Tyr Leu Lys Asn Val Lys Met Leu
 50                  55                  60
Asn Ala Lys Ser Ile Asn His Lys Ile Ser Ser Leu Ala Lys Phe Asn
 65                  70                  75                  80
Glu Phe Leu Ile Gln Lys Gly Ser Gln Gln Asp Gln Val Ile Leu Leu
                 85                  90                  95
Asp Val Lys Lys Phe Leu Gln Ser Val Leu Glu Asp Asn Asn Lys Arg
             100                 105                 110
Asn Tyr Ala Ile Ala Thr Leu Leu Ala Tyr Thr Gly Val Arg Ile Ser
         115                 120                 125
Glu Ala Leu Ser Ile Lys Met Asn Asp Phe Asn Leu Gln Thr Gly Glu
 130                 135                 140
Cys Ile Ile Arg Ser Gly Lys Gly Lys Gln Arg Ile Val Leu Leu
145                 150                 155                 160
Asn Ser Lys Val Leu Ser Ala Ile Lys Asp Tyr Leu Ile Asp Arg Lys
                 165                 170                 175
Thr Tyr Ser Thr Ala His Glu Ser Pro Tyr Leu Phe Ile Ser Lys Lys
             180                 185                 190
Arg Glu Lys Leu Asp Arg Thr Val Val Asn Arg Ile Phe Lys Ser Tyr
         195                 200                 205
Arg Asn Val Ile Thr Pro His Gln Leu Arg His Phe Phe Cys Thr Asn
 210                 215                 220
Ala Ile Gln Lys Gly Phe Ser Ile His Glu Val Ala Asn Gln Ala Gly
225                 230                 235                 240
His Ser Asn Ile His Thr Thr Leu Leu Tyr Thr Asn Pro Asn Gln Leu
                 245                 250                 255
Gln Leu Lys Asn Lys Met Glu Leu Leu
             260                 265

<210> SEQ ID NO 7
<211> LENGTH: 116
<212> TYPE: DNA
<213> ORGANISM: Bacillus thuringiensis

<400> SEQUENCE: 7
taatacaaca caatattaat tgtgttgtat taggtgttat aataaatata tatctagggg      60
tttaacgcaa cacaatttat cgataaataa atacttttag acgcaacaca atttat        116

<210> SEQ ID NO 8
<211> LENGTH: 116
<212> TYPE: DNA
<213> ORGANISM: Bacillus thuringiensis

<400> SEQUENCE: 8
taatacaaca caatattaat tgtgttgtat taggtgttat aatatatata aatctagggg      60
tttaacgcaa cacaatttat cgataaataa atacttttag acgcaacaca atttat        116

<210> SEQ ID NO 9
<211> LENGTH: 116
<212> TYPE: DNA
<213> ORGANISM: Bacillus thuringiensis
<220> FEATURE:
<221> NAME/KEY: N_region
<222> LOCATION: 33 .. 64
<223> OTHER INFORMATION: n = a, t, g, or c
<221> NAME/KEY: N_region
<222> LOCATION: 81 .. 100
<223> OTHER INFORMATION: n = a, t, g, or c
```

-continued

```
<400> SEQUENCE: 9
taatacaaca caatattaat tgtgttgtat tannnnnnnn nnnnnnnnnn nnnnnnnnnn      60
nnnnacgcaa cacaatttat nnnnnnnnnn nnnnnnnnnn acgcaacaca atttat         116

<210> SEQ ID NO 10
<211> LENGTH: 124
<212> TYPE: DNA
<213> ORGANISM: Bacillus thuringiensis
<220> FEATURE:
<221> NAME/KEY: N_region
<222> LOCATION: 33 .. 74
<223> OTHER INFORMATION: n = a, t, g, or c

<400> SEQUENCE: 10
taatacaaca caatattaat tgtgttgtat tannnnnnnn nnnnnnnnnn nnnnnnnnnn      60
nnnnnnnnnn nnnnacgcaa cacaatttac gataaataaa tacttttaga cgcaacacaa    120
ttta                                                                  124
```

US 7,083,976 B2

TYROSINE RECOMBINASE FOR GENETIC ENGINEERING

1. INTRODUCTION

The present invention is directed to methods and compositions for TnpI-mediated genetic engineering using the *Bacillus thuringiensis* recombinase TnpI and the TnpI recombination substrates TRT or TRT', and variants thereof. In particular, the invention relates to TRT or TRT' sequences, and variants thereof, vectors, cells and kits useful for TnpI-mediated genetic recombination, as well as methods for the use of TRT or TRT' sequences for TnpI-mediated genetic engineering.

2. BACKGROUND OF THE INVENTION

TnpI is a site-specific recombinase (SSR) encoded by the transposon Tn4430, a member of the TN3 family from *Bacillus thuringiensis*. TnpI belongs to the integrase family of SSRs, also referred to as the tyrosine recombinase family, and, as such, has structural similarities to other members of the integrase family of SSRs such as λ Int (Mahillon and Lereclus, 1988, EMBO J. 7:1515–26). It has been reported that TnpI mediates recombination of DNA molecules containing two relatively long DNA regions taken from Tn4430 in *Bacillus thuringiensis* (Salamitou et al., 1997, Gene 202:121–26; Sanchis et al., 1997, Appl. Environ. Microbiol. 63:779–84), and it was postulated to further require a host-derived factor (Mahillon and Lereclus, supra).

Two site-specific recombinases of the tyrosine class, Cre recombinase from the *Escherichia coli* phage P1, and Flp recombinase from the *Saccharomyces cerevisiae* 2 micron episome, have opened a new dimension in the art of intentional genetic engineering in higher eukaryotes (Kilby et al., 1993, Trends Genet. 9:413–21). Both recombinases recognize specific 34 bp recombination target sequences, called RTs. In the presence of active recombinase protein, only two corresponding RTs are required for recombination. The utility of these two recombinases lies in the fact that in both purified reactions in vitro and in living systems, other trans-acting factors or DNA sequence elements are unnecessary. By selected disposition of RTs and expression of the corresponding recombinase, precise genetic rearrangements can be effected in living cells.

Although very useful, Cre and Flp recombinases may not be suitable for many genetic engineering applications. For example, Flp originates from yeast and consequently has a thermal optimum of enzyme activity at 30° C. However, it is not very efficient at 37° C. (Buchholz et al., 1996, Nucleic Acids Res. 24:4256–62), thereby limiting its applicability in genetic engineering to those hosts that grow in the appropriate temperature range. In addition, recombination reactions catalyzed by Cre and Flp are reversible, giving rise to partially rearranged DNA molecules. Other biochemical characteristics also impinge upon recombination efficiency, again potentially limiting host range (Ringrose et al., 1998, J. Mol. Biol. 284:363–84). Thus it is important to identify new recombinases so that the genetic engineer can choose an optimal recombinase for use in the desired host organism.

Furthermore, there is great potential in genetic engineering for use of two, or more, recombinases in concert (Meyers et al., 1998, Nat. Genet. 18:136–41). However this potential has not been developed, mainly due to the absence of a suitable combination of recombinases that are efficient in a given host. Although there are now more than two hundred candidate tyrosine recombinases in the databases, it is not possible to predict which candidates will be useful for genetic engineering by protein sequence similarity alone. Many of these greater than 200 candidates probably work in multi-protein complexes and require auxiliary factors for efficient recombination. Furthermore, in many cases, their RTs are not obvious and may not be short.

Thus there is a continuing need to identify new recombinases that work efficiently on short recombination targets and do not require auxiliary factors.

Citation of a reference herein shall not be construed as an admission that such is prior art to the present invention.

3. SUMMARY OF THE INVENTION

The present invention relates to compositions and methods for site-specific recombination using the recombinase TnpI, together with TnpI recombination target sites, either in a cell or in a cell-free system. The invention encompasses methods for in vivo and in vitro TnpI-mediated site-specific recombination, nucleic acid molecules, host cells and vectors that may be employed in such methods, and kits for use with such methods, nucleic acid molecules, host cells, and vectors.

The present invention is based on the discovery by the inventors of novel properties of TnpI and TnpI recombination target sites which are useful for genetic engineering. First, TnpI mediates recombination at two functionally distinct TnpI recombination target sites, herein identified as TRT and TRT'. TRT, the minimum 'core' TnpI recombination target site consists of a 32 bp recombination target (RT) site, comprising two inverted repeat sequences. The larger TRT' is a 116 bp sequence comprising the core TRT as well as two direct repeat sequences. Second, TnpI mediated site-specific recombination using TRT and TRT' substrates can be accomplished both in vitro and in vivo, without requiring any auxiliary factors. These previously unknown abilities of TnpI and its recombination substrates (referred to herein as the TnpI/TRT system) result in useful properties for genetic engineering.

In one embodiment, the invention provides a composition comprising an isolated DNA molecule comprising one or more copies of TRT (SEQ ID NO:3) or a functional variant thereof, with the proviso that the DNA molecule does not comprise the entire sequence of TRT" (SEQ ID NO:4). In a specific embodiment, the DNA molecule comprises one or more copies of TRT (SEQ ID NO:3), or a functional variant thereof, and a heterologous nucleotide sequence. In other specific embodiment, the DNA molecule does not comprise more than 32, 50, 100, 150, or 200 contiguous nucleotides of the sequence of TRT" (SEQ ID NO:4). In another embodiment, the DNA molecule further comprises a selectable marker. In another embodiment, the DNA molecule is a vector.

In another embodiment, the invention provides a composition comprising an isolated DNA molecule comprising one or more copies of TRT' (SEQ ID NO:2), or a functional variant thereof, with the proviso that the DNA molecule does not comprise the entire sequence of TRT" (SEQ ID NO:1). In a specific embodiment, the DNA molecule comprises one or more copies of TRT' (SEQ ID NO:2), or a functional variant thereof, and a heterologous nucleotide sequence. In various specific embodiments, the DNA molecule comprises one or more copies of TRT' (SEQ ID NO:2), or a functional variant thereof, with the proviso that the DNA molecule does not comprise more than 116, 125, 150, 175, or 200 contiguous nucleotides of the sequence of TRT" (SEQ ID NO:4). In another embodiment, the DNA molecule further comprises a selectable marker. In another embodiment, the DNA molecule is a vector.

In another embodiment, the invention provides a cell transformed with a DNA molecule, said DNA molecule comprising one or more copies of TRT (SEQ ID NO:3), or a functional variant thereof, with the proviso that the DNA molecule does not comprise the entire sequence of TRT" (SEQ ID NO:4). In another embodiment, the invention further provides a cell transformed with a DNA molecule, said DNA molecule comprising one or more copies of TRT' (SEQ ID NO:2), or a functional variant thereof, with the proviso that the DNA molecule does not comprise the entire sequence of TRT" (SEQ ID NO:4). In specific embodiments, the DNA molecule is integrated into the chromosome of the cell.

The invention further provides a eukaryotic cell transformed with a DNA molecule integrated into its chromosome, said DNA molecule comprising one or more copies of TRT (SEQ ID NO:3) or a functional variant thereof, or TRT' (SEQ ID NO:2), or a functional variant thereof. In a specific embodiment, the cell is a mouse embryonic stem cell. In a specific embodiment, the DNA molecule comprises two copies of TRT' (SEQ ID NO:3), or a functional variant thereof, separated by a heterologous nucleotide sequence. In another embodiment, the DNA molecule comprises two copies of TRT' (SEQ ID NO:2), or a functional variant thereof, separated by a heterologous nucleotide sequence.

The invention further provides kits for use of the TnpI/Trt system for genetic engineering. In one embodiment, a kit comprising in one or more containers: a) an isolated DNA molecule comprising one or more copies of TRT (SEQ ID NO:3) or a functional variant thereof; and b) an isolated TnpI protein, a TnpI expression vector or a cell capable of expressing TnpI. In another embodiment, a kit is provided comprising in one or more containers: a) an isolated DNA molecule comprising one or more copies of TRT' (SEQ ID NO:2) or a functional variant thereof; and b) an isolated TnpI protein, a TnpI expression vector or a cell capable of expressing TnpI.

The invention further provides methods for use of the TnpI/Trt system for genetic engineering. In one embodiment, a method is provided for effecting TnpI-mediated site-specific recombination comprising exposing a first TnpI recombination target site and a second TnpI recombination target site with TnpI protein, under sufficient conditions and in an amount sufficient to mediate site-specific recombination between the first and second TnpI recombination target sites, wherein the first and second TnpI recombination target sites are selected from the group consisting of TRT (SEQ ID NO:3) or a functional variant thereof, and TRT' (SEQ ID NO:2) or a functional variant thereof, with the proviso that the DNA molecule does not comprise the entire sequence of TRT" (SEQ ID NO:4).

In a specific embodiment of this method, site-specific recombination occurs in vitro. In another specific embodiment, the site-specific recombination occurs in a cell. In one embodiment, the cell is a non-*Bacillus thuringiensis* cell. In another embodiment, the cell is not a Gram positive cell. In another embodiment, the first TnpI recombination target site and the second TnpI recombination target site are on different DNA molecules. In yet another embodiment, the first TnpI recombination target site and the second TnpI recombination target site are on the same DNA molecule. In one embodiment of this method, the DNA molecule is chromosomal DNA. In another embodiment, the first TnpI recombination target site and the second TnpI recombination target site are in direct orientation. In another embodiment, the DNA molecule further comprises one or more non-TnpI site-specific recombination target sites. In another embodiment, at least one of the one or more non-TnpI sites is a Cre recombinase target site. In another embodiment, at least one of the one or more non-TnpI sites is a Flp recombinase target site. In another embodiment, the DNA molecule comprises, in the following order, from 5' to 3', the first TnpI recombination target site, a heterologous nucleotide sequence, and the second TnpI recombination target site.

The invention further provides a method for effecting site-specific recombination in a non-*Bacillus thuringiensis* cell comprising exposing a first TnpI recombination target site and a second TnpI recombination target site to TnpI protein, under sufficient conditions and in an amount sufficient to mediate site-specific recombination between the first TnpI recombination target site and second TnpI recombination target site, wherein the first and second TnpI recombination target sites are selected from the group consisting of TRT (SEQ ID NO:3) or a functional variant thereof, and TRT' (SEQ ID NO:2) or a functional variant thereof. In one embodiment, this method further comprising, before said exposing, a step of introducing into the cell a first TnpI recombination target site and a second TnpI recombination target site. In another embodiment, the first TnpI recombination target site and the second TnpI recombination target site are on different DNA molecules. In an alternative embodiment, the first TnpI recombination target site and the second TnpI recombination target site are on the same DNA molecule. In another embodiment, the first TnpI recombination target site and the second TnpI recombination target site are in direct orientation. In another embodiment, the DNA molecule further comprises one or more non-TnpI site-specific recombination target sites. In yet another embodiment, at least one of the one or more non-TnpI sites is a Cre recombinase target site. In another embodiment, at least one of the one or more non-TnpI sites is a Flp recombinase target site. In a specific embodiment, the DNA molecule further comprises a heterologous nucleotide sequence, in the following order, from 5' to 3', the first TnpI recombination target site, a heterologous nucleotide sequence, and the second TnpI recombination target site, such that recombination between the first and the second TnpI recombination target site results in deletion of the heterologous nucleotide sequence. In another specific embodiment, the first TnpI recombination target site and the second TnpI recombination target site are in inverse orientation. In another specific embodiment, the cell contains a sequence encoding TnpI operably linked to a promoter. In another embodiment, the promoter is an inducible or tissue-specific promoter. In another specific embodiment, the cell is a eukaryotic cell, e.g., a mouse cell or an embryonic stem cell. In another specific embodiment, the first TnpI recombination target site and the second TnpI recombination target site are both TRT' sequences (SEQ ID NO:2) or functional variants thereof. In another embodiment, the first TnpI recombination target site and the second TnpI recombination target site are both TRT sequences (SEQ ID NO:3) or functional variants thereof.

The invention further provides a method of producing a circular DNA vaccine comprising: (a) introducing a DNA molecule into a non-*Bacillus thuringiensis* cell, said DNA molecule comprising, in the following order, from 5' to 3', a DNA sequence encoding an antigen of interest, a first TRT' site or functional variant thereof, an origin of replication and, optionally, one or more selectable markers, and a second TRT' site or functional variant thereof; and (b)

contacting said cell with TnpI protein under sufficient conditions and in an amount sufficient to mediate site-specific recombination between the first and second TRT' sites or functional variants thereof, such that recombination between the first and the second TRT' sites or functional variants thereof results in deletion of the origin of replication and the optional one or more selectable markers from the DNA molecule, such that a circular DNA vaccine encoding an antigen of interest is produced.

As used herein, the term "functional variant" of a TRT or TRT' sequence refers to a TRT or TRT' sequence with one or more altered nucleotide residues, such that the TRT or TRT' functional variant, when contained in a DNA molecule with a TRT or TRT', is capable of acting as a substrate for TnpI-mediated recombination, as assayed by an in vivo or an in vitro TnpI-mediated recombination assay. As used herein, the term "heterologous nucleotide sequence" refers to a non-Tn4430 nucleotide sequence.

4. DESCRIPTION OF THE FIGURES

FIGS. 1A–C. TnpI recognition target sequences.

1A. TRT" [SEQ ID NO:1], a 244 bp fragment containing a direct repeat of the sequence AAAATCAGA (nucleotides 37–45 and 51–59 of SEQ ID NO:1), an inverted repeat of the sequence TAATACAACACAAT (nucleotides 111–124 of SEQ ID NO:1), and a direct repeat of the sequence ACGCAACACAATTTAT (nucleotides 175–190 and 211–226 of SEQ ID NO:1).

1B. A 134 bp fragment [SEQ ID NO:11] containing as the first 116 nucleotides TRT' [SEQ ID NO:2], a 116 bp fragment containing an inverted repeat of the sequence TAATACAACACAAT (nucleotides 1–14 of SEQ ID NO:2 and of SEQ ID NO:11) and a direct repeat of the sequence ACGCAACACAATTTAT (nucleotides 65–80 and 101–116 of SEQ ID NO:2 and of SEQ ID NO:11).

1C. TRT [SEQ ID NO:3], a 32 bp fragment containing an inverted repeat of the sequence TAATACAACACAAT (nucleotides 1–14 of SEQ ID NO:3).

FIGS. 2A–B. Sequence and structure of the transposon Tn4430

2A. A schematic diagram of the transposon Tn4430, with its 38 bp terminal inverted repeats (IR) represented by triangles and the position of the TnpI and TnpA (transposase) coding regions depicted as grey arrows.

2B. Sequence of the 249 bp TRT" [SEQ ID NO:4] indicating the following: the Tn4430 left IR (first shaded box); TnpI binding regions (open boxes), within which is shown the inverted repeats (black arrows), and the conserved 9 bp sequence (5'-CAACACAAT-3') common to all four TnpI binding sites; the direct repeats (grey arrows); and the TnpI translational start site (second shaded box).

FIG. 3. The coding nucleotide sequence [SEQ ID NO:5] and the deduced amino acid sequence [SEQ ID NO:6] of TnpI'.

Figure 4:
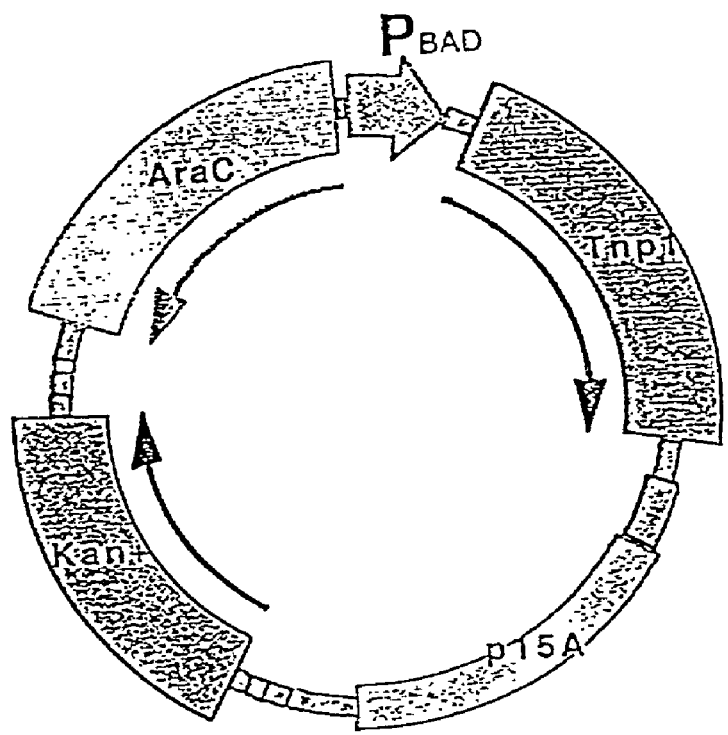

FIG. 4. TnpI expression vector pYZ-BAD-TnpI, comprising a p15A replication origin, a kanamycin selection marker, arabinose-inducible promoter $P_{BAD}$, and AraC, the arabinose-responsive repressor that regulates $P_{BAD}$.

FIG. 5. TnpI-mediated recombination in E. coli.

5A. Schematic representation of TnpI recombination substrate and products. The circular DNA starting material substrate (S) containing two directly repeated TnpI recombination target sites (arrows) and an origin of replication (filled circles). Recombination between the two TnpI recombination target sites produces two circular products (P), only one of which contains the origin of replication and is therefore capable of replicating in the cell.

5B. Agarose gel of products of TnpI-mediated recombination in E. coli. Plasmids contained either TRT or TRT' grown in E. coli, in either the presence (+) or absence (–) of TnpI expression. Lane 1: size marker. Lane 4: Plasmid containing TRT'-flanked sequence in the absence of TnpI. Lane 5: TRT'-containing plasmid recombination products after recombination by TnpI (excised fragment lost during cell division). Lane 6: Plasmid containing TRT-flanked sequence in the absence of TnpI. Lane 7: TRT-containing plasmid recombination products after recombination by TnpI. (Lanes 2 and 3 are irrelevant.) Note high-molecular weight products not seen in the TRT'-containing plasmid. Positions of DNA fragments corresponding to the starting material substrate (S) and recombination products (P) are indicated to the left of gel.

FIG. 6. Overexpression and purification of TnpI.

6A. Schematic representation of the relevant portions of the pGIV007 and pGIV008 expression vectors showing the pBAD::His-tag::tnpI and the pBAD::tnpI genes, respectively. Positions of the start codons (ATG), the ribosome binding sites (RBS), and the restriction sites NcoI are indicated.

6B. SDS-polyacrylamide gel electrophoresis showing the elution profile of the H-TnpI (top) and the TnpI (bottom) proteins from the nickel resin. The different lanes correspond to fractions that eluted at increased concentrations of imidazole as indicated. Arrowheads show the position of the H-TnpI and TnpI proteins.

FIG. 7. TnpI-mediated recombination in vitro.

7A. Schematic representation of the circular DNA substrate carrying directly repeated TRT (PGIV016) or TRT' (PGIV014) recombination sites (arrows). Recombination gives two circular products (P1 and P2) that can be distinguished from the substrate by restriction with HindIII (HdIII).

7B. Agarose gel (0.8%) of recombination reactions in the presence (+) or absence (–) of H-TnpI using, as substrates, plasmids carrying two copies of TRT (pGIV016, left panel) or TRT' (pGIV014, right panel). Positions of DNA fragments corresponding to the substrates (S1 and S2) and recombination products (P1 and P2) are indicated.

7C. Kinetics of recombination at TRT (squares) and TRT' (diamonds).

Figure 8:
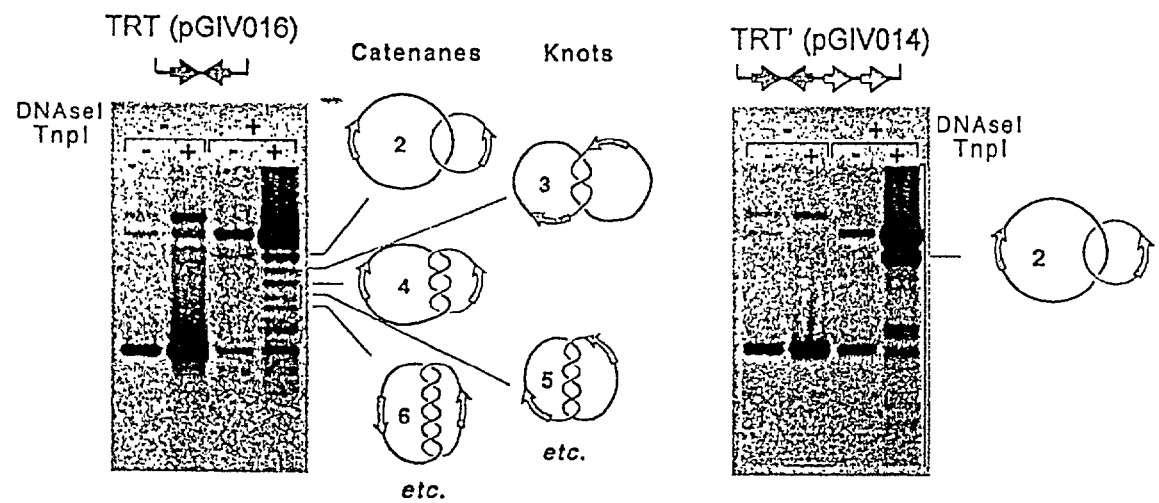

FIG. 8. Topology of TRT and TRT' recombination reactions. Plasmid substrates incubated in the presence (+) or absence (–) of H-TnpI, and then treated in the presence (+) or absence (–) of DNase I, as indicated.

8A. Agarose gel (0.7%) of TRT recombination products, yielding a DNase I ladder of catenanes containing 2, 4, 6, etc. nodes (shown to the right). Faint bands correspond to knotted products arising from multiple rounds of recombination.

8B. Agarose gel (0.7%) of TRT' recombination products yielding a unique 2-noded catenane product.

Figure 9:
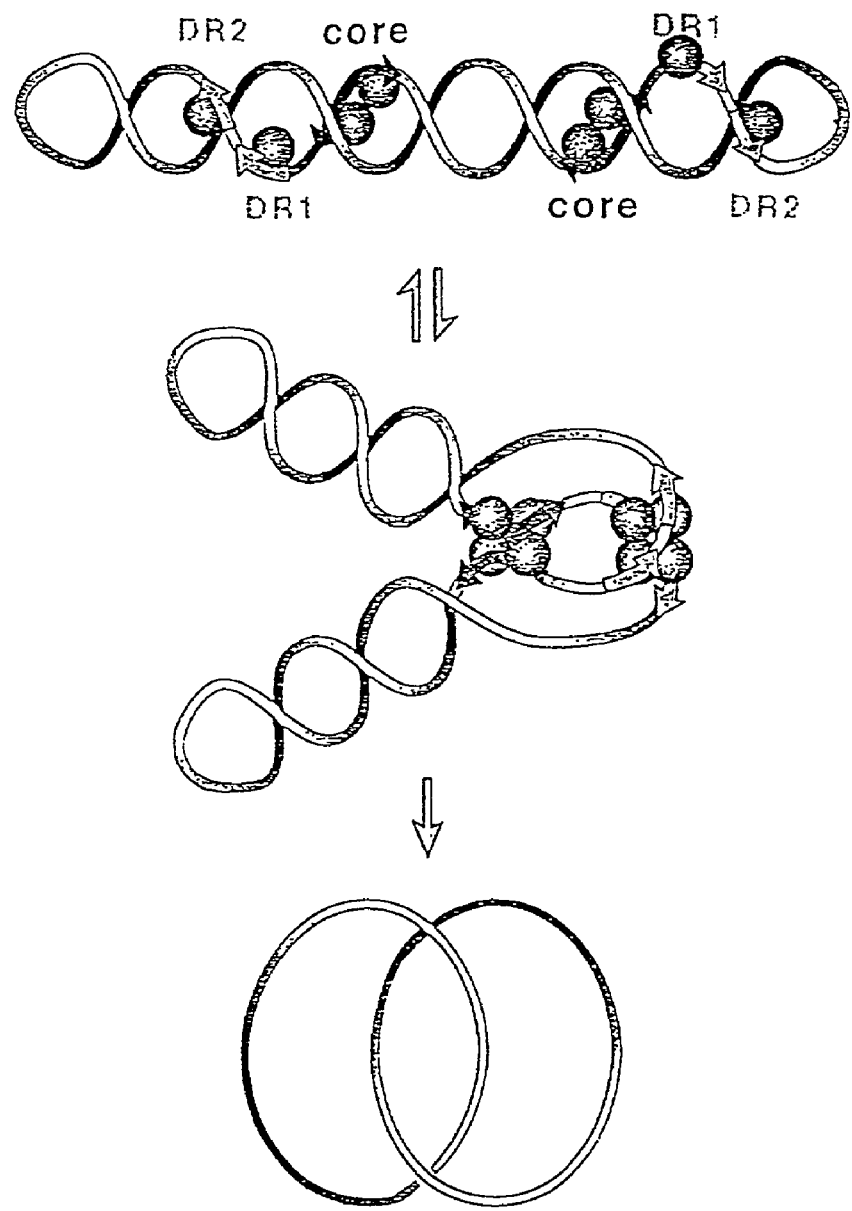

FIG. 9. Representation of a TnpI-TRT' complex. "Core"=TRT. "DR1" and "DR2"=direct repeat 1 and direct repeat 2.

Figure 10:
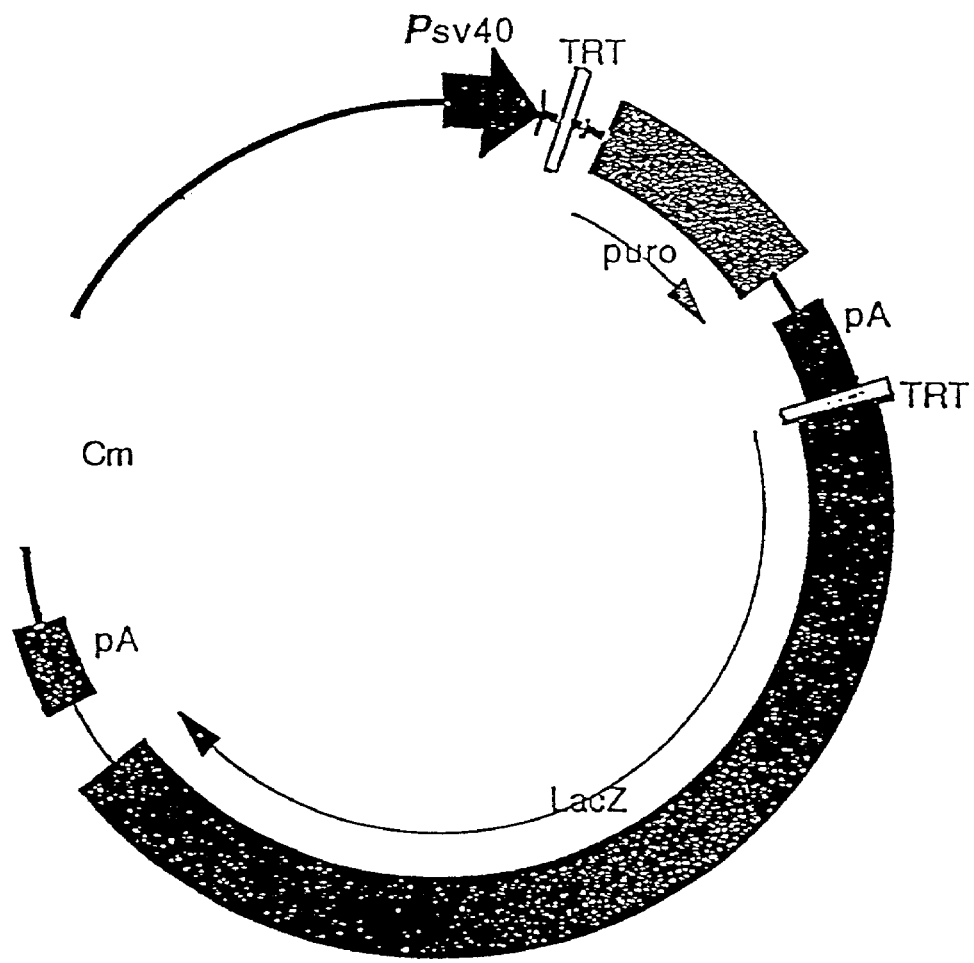

FIG. 10. Vector pSVpaT, comprising the SV40 promoter $p_{SV40}$, a puromycin resistance gene puro flanked by two 32 bp TRT sequences, the β-galactosidase gene LacZ, and a chloramphenicol resistance gene cm. pA indicates a polyadenylation signal.

Figure 11:
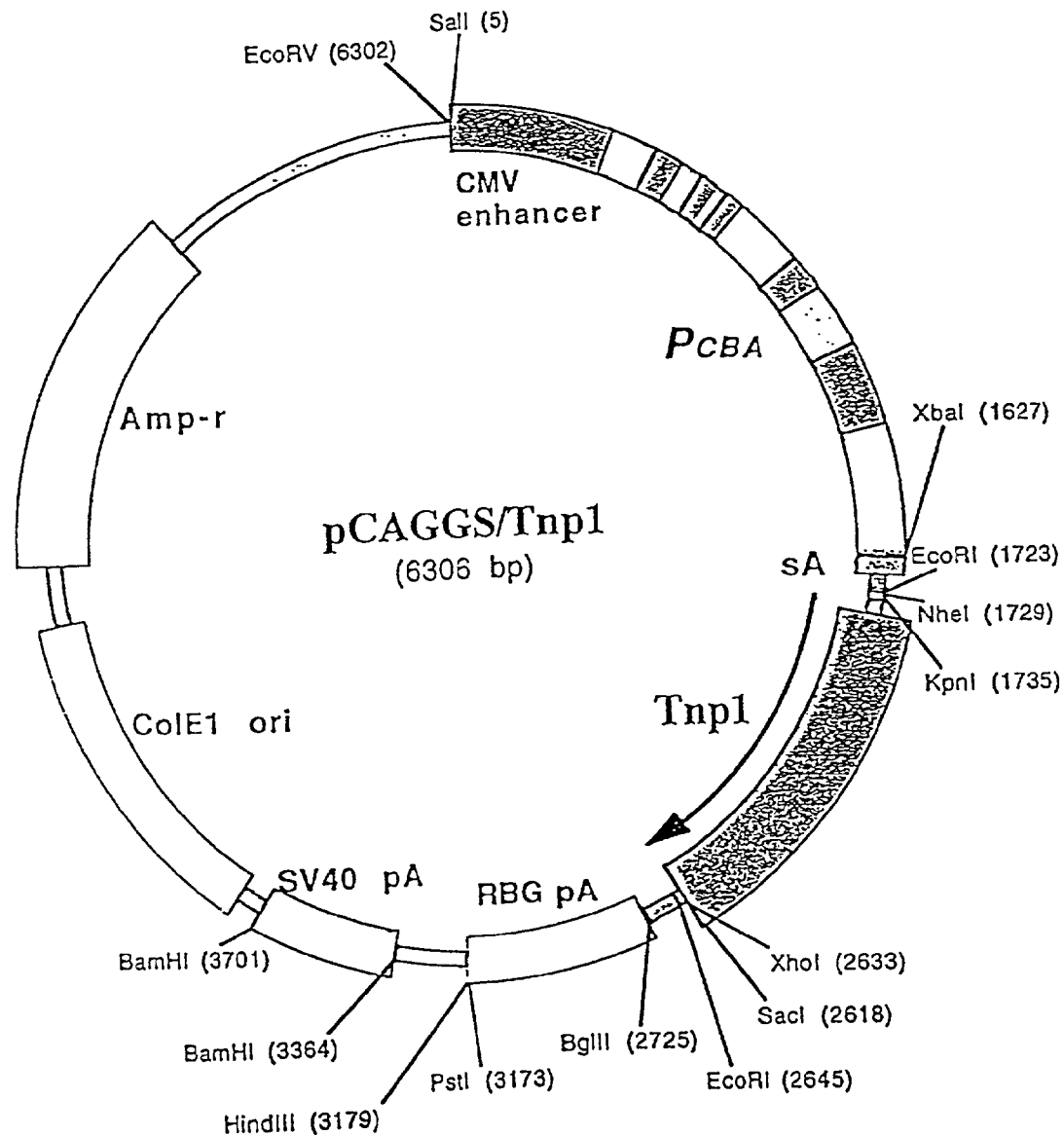

FIG. 11. Plasmid pCAGGS/TnpI, used to express TnpI in eukaryotic cells, comprises the constitutive chicken beta-actin promoter P$_{CBA}$, the rabbit beta-globin polyA-encoding sequence RBG pA, and splicing acceptor site sA.

Figure 12:
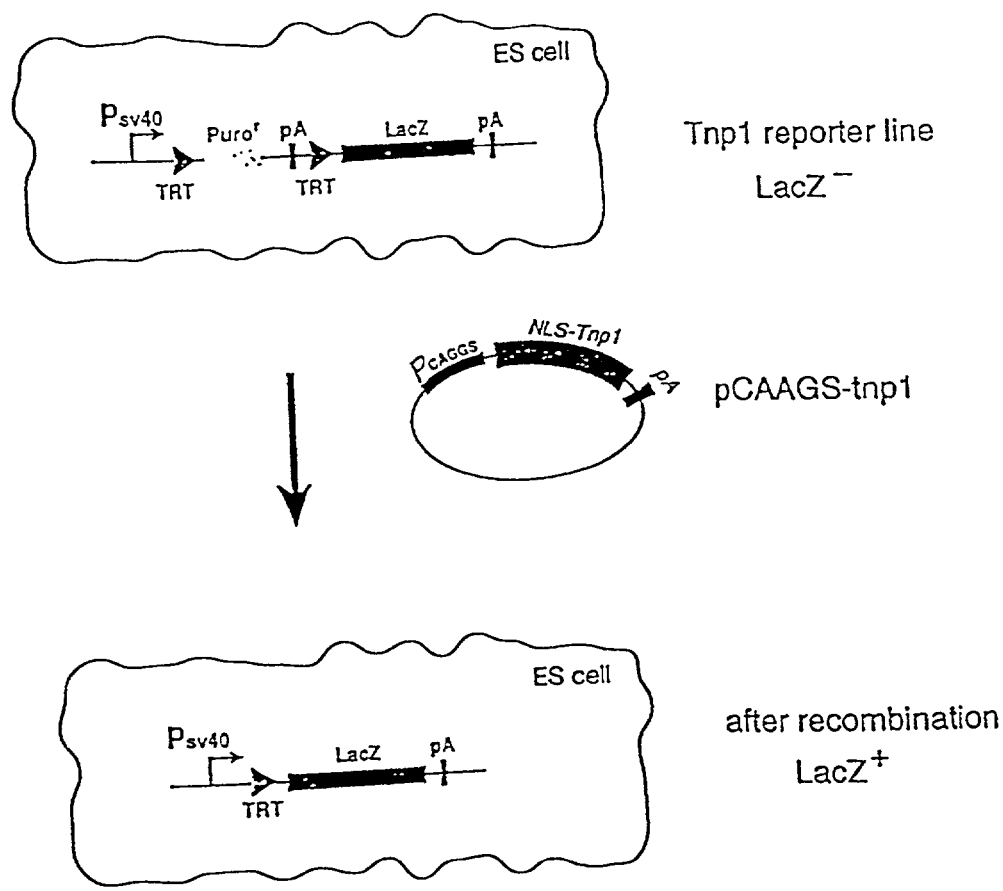

FIG. 12. TnpI-mediated recombination in eukaryotic cells. Diagram of the mouse ES reporter cell system cassette (top panel), containing a puromycin resistance gene, puro, flanked by TRT recombination target sites, and a non-expressed lacZ gene. Upon expression of TnpI from the plasmid pCAGGS/TnpI, the puromycin resistance gene is excised and the lacZ gene placed under the control of the P$_{SV40}$ promoter and expressed (bottom panel).

Figure 13:
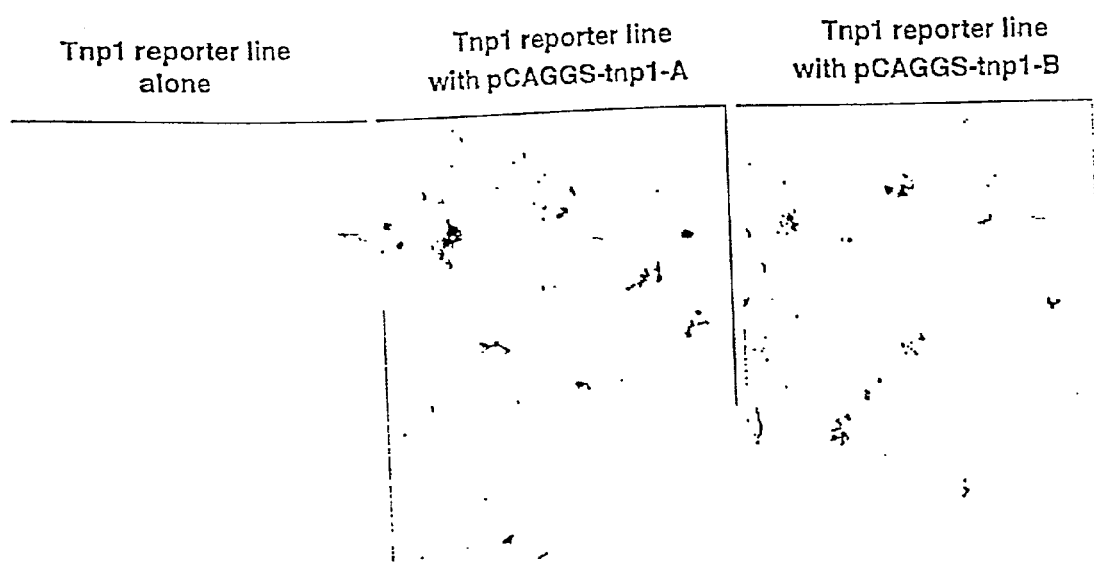

FIG. 13. LacZ assay of mouse ES reporter cells expressing TnpI from pCAGGS/TnpI. LacZ is expressed only when active TnpI is expressed within the ES reporter cell lines, as indicated by the dark (blue) cells.

5. DETAILED DESCRIPTION OF THE INVENTION

The present invention is directed to compositions and methods for TnpI recombinase-mediated genetic engineering. As discussed above, TnpI is a site-specific recombinase (SSR) encoded by the *B. thuringiensis* transposon Tn4430 (Mahillon and Lereclus, supra). Although previously thought to require a host-derived factor for functionality, as demonstrated herein, TnpI requires only its specific recognition sequence contained in Tn4430 to mediate recombination.

The invention is based on the discovery by the inventors of the following novel properties of TnpI and its recombination target sites. First, TnpI mediates recombination at two functionally distinct TnpI recombination target sites, herein identified as TRT and TRT'. TRT, a 32 bp recombination target (RT) site (shown in FIG. 1C and described in detail below), includes two inverted repeat sequences, the minimum 'core' recombination site. The larger TRT' is a 116 bp sequence, comprising the core TRT as well as two direct repeat sequences (shown in FIG. 1B and described in detail below). As described more fully hereinbelow, both the recombination outcome and efficiency at these sites are different. For example, recombination between two TRT sequences is 'unconstrained' (or 'relaxed') because it occurs freely between recombination sites, giving rise to all possible inter- and intramolecular DNA rearrangements in vivo, and a variety of topological products in vitro. In contrast, the direct repeats of the larger TRT' constrain recombination by preventing intermolecular recombination events and favoring intramolecular deletion reactions between directly repeated sites. This 'constrained', unidirectional recombination leads to the excision of sequences lying between the two TRT' sites. This previously unknown ability of the TnpI recombinase to mediate recombination reactions with different outcomes as a function of the structure of its recombination site is an unprecedented and useful feature for genetic engineering.

Second, TnpI mediated site-specific recombination using TRT and TRT' substrates can be accomplished both in vitro and in vivo, without requiring any auxiliary factors. Thus, for example, TnpI mediated site-specific recombination can be used in eukaryotic cells, such as, for example, mouse embryonic stem cells ("ES cells").

Described herein are compositions and methods relating to the use of TnpI with these two TnpI recombination targets (also referred to herein as the TnpI/TRT system). The present invention relates to methods for the use of the TnpI/TRT system in eukaryotic or prokaryotic, non-*B. thuringiensis* hosts, the use of TRT and TRT' in conjunction with expressed TnpI to accomplish genetic rearrangements, including excisions from vectors and from cellular DNA, vectors and combinations of vectors to accomplish those excisions, and kits utilizing those vectors, cells, and methods. In particular, Section 5.1 describes compositions of the invention, including DNA constructs designed for site-specific recombination events using TnpI and a recombination target, and kits comprising such constructs. Section 5.2 describes methods for use of the invention, including methods for manipulation, excision, and integration of genes of interest into prokaryotic or eukaryotic host genomic DNA using TnpI and various genetic constructs that include a recombination target.

5.1 Compositions for TnpI-mediated Site-specific Recombination

Compositions comprising TnpI recombination target sequences useful for genetic engineering, including TRT', TRT, and sequence variants thereof, are described in detail herein.

First, the invention encompasses the minimum core recombination site TRT,

5'-<u>TAATACAACACAAT</u>[ATTA]<u>ATTGTGTTGTATTA</u>, [SEQ ID NO:3]

a 32 bp sequence comprising a pair of inverted repeats (underlined), also shown in FIG. 1C. Recombination occurs by a TnpI staggered cleavage at symmetrical positions within this sequence, between the last two nucleotides at the 3' end of the repeat (i.e., CACAA/T), resulting in a 6 bp central sequence, TATTAA), referred to herein as the 'central crossover region'.

The invention further encompasses the larger TRT', a 116 bp sequence comprising a the core TRT site and a pair of direct repeats (bolded):

[SEQ ID NO:2]
5'-<u>TAATACAACACAAT</u>[ATTA]<u>ATTGTGTTGTATTA</u>GGTG

TTATAATAAATATAAATCTAGGGGTTTAACGCAACA

CAATTTATCGATAAATAAATACTTTTAGACGCAACA

CAATTTAT, which is depicted in FIG. 1B.

Both TRT and TRT' are sequences contained entirely within the Tn4430 left IR shown in FIG. 1A (referred to herein as TRT"). In one embodiment, the invention further encompasses a DNA molecule comprising one or more copies of the TRT site, providing the DNA molecule does not comprise the entire sequence of TRT". In a preferred embodiment, the DNA molecule consists of the TRT site and additional nucleotide sequences, providing the additional sequence does not comprise more than 216 contiguous nucleotides of TRT". Preferably, the additional nucleotide sequence comprises not more than 2, 5, 10, 20, 30, 40, 50, 100, 150, or 200 contiguous nucleotides of TRT".

In another embodiment, the invention further encompasses a DNA molecule comprising one or more copies of the TRT' site, providing the DNA molecule does not comprise the entire sequence of TRT". In a preferred embodiment, the DNA molecule consists of the TRT' site and additional nucleotide sequences, providing the additional sequence does not comprise more than 132 contiguous nucleotides of TRT". Preferably, the additional nucleotide sequence comprises not more than 2, 5, 10, 20, 30, 40, 50, or 100 contiguous nucleotides of TRT".

In a preferred embodiment, the invention encompasses a composition comprising a DNA molecule consisting of one or more copies of TRT and a heterologous nucleotide sequence. In another preferred embodiment, such a composition comprises a DNA molecule consisting of one or more copies of TRT' and a heterologous nucleotide sequence. As used herein, the term "heterologous nucleotide sequence" refers to a non-Tn4430 nucleotide sequence.

The invention further encompasses functional variants of TRT or TRT' sequences. As used herein, the term "functional variant" of a TRT or TRT' sequence refers to a TRT or TRT' sequence with one or more altered nucleotide residues, such that the TRT or TRT' functional variant, when contained in a DNA molecule with a TRT or TRT', is capable of acting as a substrate for TnpI-mediated recombination, as assayed by an in vivo or an in vitro TnpI-mediated recombination assay. Such a TRT or TRT' functional variant sequence may be constructed by modifying the identity of one or more nucleotides between or within the core TRT site, or in the case of a variant TRT' sequence, within the accessory direct repeats or the TRT' spacer region between the core TRT site and the first accessory direct repeat (referred to herein as the "spacer region"). Such functional variants may be single point mutations, double point mutations, or multiple point mutations, insertions and/or deletions, and may be constructed using routine methods well known in the art (see, e.g., Sambrook et al., 1989, Molecular Cloning—A Laboratory Manual, 2nd Edition, Cold Spring Harbor Press, New York).

For example, in various embodiments, sequences which may be altered include, but are not limited to, the TnpI binding sites, of the TRT central crossover region, or sequences within the TRT' spacer region. Such functional variant TnpI recombination target sequences may then be tested for Tnp1 binding and recombination activity in vivo or in vitro, in the various assays described in detail herein. In a preferred embodiment, such assays are used to select for functional variant TnpI recombination target sequences with increased binding affinity and/or recombination activity.

In one embodiment, for example, a TRT' functional variant is constructed comprising one or more altered nucleotide residues within the spacer region, which preserves the sequence of the core TRT site and the accessory direct repeats themselves. Such a functional variant TRT' sequence may then be tested for recombination activity in vivo or in vitro, as described herein. For example, in one embodiment, such a functional variant TRT' sequence comprises the following sequence:

[SEQ ID NO:7]
5'-TAATACAACACAAT[ATTA]ATTGTGTTGTATTAGGTG

TTATAATAAATATATATCTAGGGGTTTAACGCAACA

CAATTTATCGATAAATAAATACTTTTAGACGCAACA

CAATTTAT wherein the altered nucleotide residue is underlined and in bold.

In another embodiment, a functional variant TRT' sequence comprises the following sequence:

[SEQ ID NO:8]
5'-TAATACAACACAAT[ATTA]ATTGTGTTGTATTAGGTG

TTATAATATATATAAATCTAGGGGTTTAACGCAACA

CAATTTATCGATAAATAAATACTTTTAGACGCAACA

CAATTTAT, wherein the altered nucleotide residue is underlined and in bold.

In general, such a functional variant TRT' sequence may have the following general sequence:

[SEQ ID NO:9]
5'-TAATACAACACAAT[ATTA]ATTGTGTTGTATTA[X$_{32}$]A

CGCAACACAATTTAT[X$_{20}$]ACGCAACACAATTTAT, wherein X represents a nucleotide residue.

In another embodiment, a functional variant TRT' sequence may be constructed by modifying the length of the spacer between the core TRT site and the accessory direct repeats. For example, the spacer may be modified by the addition of one integral helical turn of the DNA helix, i.e., 10 bp, or a multiple thereof, i.e., 21 or 31 bp, for example. In one embodiment, for example, nucleotide sequences having the following consensus sequence may be used as TnpI recombination targets:

[SEQ ID NO:10]
5'- TAATACAACACAAT[ATTA]ATTGTGTTGTATTA[X$_{42}$]A

CGCAACACAATTTACGATAAATAAATACTTTTAGAC

GCAACACAATTTA, wherein the underlined nucleotide residues depict the inverted repeats, bolded nucleotide residues represent direct repeats, and X$_{42}$, represents a spacer region sequence comprising an additional integral helical turn between the core TRT site and the accessory direct repeats.

Preferably, the accessory direct repeats are tenderly repeated on a same DNA molecule as the core TRT site. In another embodiment, the orientation of the direct repeats within the recombination target site may be manipulated. Reorienting the direct repeats can result in more complete removal of TRT sequences, which may be advantageous to genetic engineering applications. In alternative embodiments, for example, the orientation of the direct repeats may be forward, as depicted above, or reversed ("flipped") with respect to the inverted repeats.

The invention further comprises compositions with more than one copy of a TnpI recombination target sequence, such as TRT', TRT, or a functional variant thereof, on a single DNA molecule. Preferably, the DNA molecule comprises two TnpI recombination target sequences in tandem, separated by a variable length of heterologous sequence, recombination may occur between such TnpI recombination target sites. In one embodiment, such a DNA molecule comprises two TnpI recombination target sites, such as TRT', TRT, or a functional variant thereof, in direct repeat orientation. In another embodiment, such a DNA replicon comprises two TnpI recombination target sites, such as TRT', TRT, or a functional variant thereof, in inverted repeat orientation.

5.1.1 TnpI Recombination Target Vectors

Vectors comprising TnpI recombination targets may be constructed. TnpI recombination target sites may be separated from each other by a nucleotide sequence, such as a nucleotide sequence encoding a selectable marker, or a nucleotide sequence encoding a gene of interest, such that recombination between the target sequence deletes or inverts the nucleotide sequence located between the two TnpI recombination targets.

In one embodiment, the vector comprises, in order: (1) a promoter; (2) a first TRT'; (3) a multiple cloning site (MCS); and (4) a second TRT', wherein the first and second TRT's flank the MCS. The MCS includes restriction enzyme cleavage sites that will enable the cloning of nucleotide sequences such that those sequences are controlled by the promoter. Upon introduction of the vector into a cell, and under the appropriate conditions, the nucleotide sequence cloned into the MCS will be expressed. Expression is terminated upon expression of TnpI in the cell from a different vector. Such a system may be desirable in situations in which the first vector contains a constitutive promoter, or when it is not feasible to remove the inducing factor regulating an inducible promoter.

In another embodiment, the vector comprises, in order: (1) a promoter; (2) a first TRT'; (3) a spacer sequence that prevents the promoter from controlling the expression of downstream sequences; (4) a second TRT'; and (5) a gene of interest. Upon TnpI-mediated recombination, the spacer sequence is excised, allowing the promoter to control expression of the gene of interest. In this embodiment, the promoter may be constitutive, or, preferably, inducible.

Such vectors will have the general characteristics outlined in Section 5.1.3, below. Vectors carrying recombination targets in such a manner may either be designed to exist as episomes, or may be designed to facilitate integration into the host genomic DNA to create stable cell lines, e.g., by designing vector to be linearized. Such vectors are known in the art.

5.1.2 TnpI Expression Vectors

Vectors that express TnpI can be used as episomes to confer upon the host cell the ability to express TnpI. Such vectors, which may be a prokaryotic or eukaryotic expression vectors, will have the general characteristics of vectors as described in Section 5.1.1, above. The ability to generate a wide range of expression is advantageous for utilizing the methods of the invention. Such expression can be achieved in a constitutive as well as in a regulated, or inducible, fashion. A variety of regulatory sequences which allow expression (either regulated or constitutive) at a range of different expression levels are well known to those of skill in the art.

It may be desirable to express TnpI as either a native TnpI or, alternatively, as a fusion protein. For example, in one embodiment, TnpI may be expressed as a fusion protein with the TnpI coding sequence linked to a detectable peptide, such a His-tag fusion protein to facilitate detection or purification. In another embodiment, TnpI may be expressed as a fusion protein with a peptide which imparts a functional group, such as a nuclear localization signal, a hormone receptor domain, etc. A variety of peptides useful for constructing such fusion proteins, and methods for their construction, are well known in the art.

In a specific embodiment, a vector is used that comprises an inducible promoter operably linked to a TnpI-encoding nucleic acid, one or more origins of replication, and, optionally, one or more selectable markers (e.g., an antibiotic resistance gene). In another embodiment, a vector is used that comprises a tissue-specific promoter operably linked to a TnpI-encoding nucleic acid, one or more origins of replication, and, optionally, one or more selectable markers.

The chosen vector must be compatible with the vector plasmid described in Section 5.1.1, above. One of skill in the art would readily be aware of the compatibility requirements necessary for maintaining multiple plasmids in a single cell. Methods for propagation of two or more constructs in procaryotic or eukaryotic cells are well known to those of skill in the art. For example, cells containing multiple replicons can routinely be selected for and maintained by utilizing vectors comprising appropriately compatible origins of replication and independent selection systems (see Miller, 1992, A Short Course in Bacterial Genetics, Cold Spring Harbor Laboratory Press, NY, and references therein; and Sambrook et al., 1989, supra).

5.1.3 Vectors Generally

Circular vectors incorporating a TnpI coding region, or a region to be manipulated by TnpI, may be constructed using standard methods known in the art (see Sambrook et al., 1989, supra; Ausubel et al., Current Protocols in Molecular Biology, Greene Publishing Associates and Wiley Interscience, New York). For example, synthetic or recombinant DNA technology may be used. In one embodiment, a TnpI coding fragment is made by polymerase chain reaction ("PCR") amplification. In this method, oligonucleotides are synthesized to include restriction enzyme sites at their 5' ends, and PCR primer sequences complementary to the boundary sequences of a TnpI coding region at their 3' ends. These oligonucleotides are then used as primers in a PCR amplification reaction to amplify the TnpI coding region. This amplified region is then cloned into a vector containing an equivalent restriction site downstream of a promoter in such a manner that the promoter controls expression of the TnpI coding sequence. In another embodiment, a plasmid may be constructed to comprise two appropriately oriented TRTs or TRT's flanking a gene segment to be excised or inverted, using standard molecular biology techniques (see e.g., Methods in Enzymology, 1987, Volume 154, Academic Press; Sambrook et al., 1989, supra; and Ausubel et al., supra). The circular product is then transformed into *Escherichia coli* for amplification to yield large amounts of the vector.

As TnpI-mediated recombination may be used in either prokaryotic or eukaryotic systems, the choice of vector construction depends upon the cell line or bacterial strain under study. For prokaryotic systems, the vector preferably includes an appropriate origin of replication and one or more selectable markers. For example, in plasmids maintained and used in *E. coli*, examples of appropriate origins of replication would be, without limitation, ColE1-derived origins of replication (Bolivar et al., 1977, Gene 2:95–113; see Sambrook et al., 1989, supra), p15A origins present on plasmids such as pACYC184 (Chang and Cohen, 1978, J. Bacteriol. 134:1141–56; see also Miller, 1992, supra, p. 10.4–10.11), and pSC101 origin. Origins of replication may be selected for high (see Sambrook et al., 1989, supra; see also Miller, 1992, supra, and references therein), medium (Bolivar et al., 1977, Gene 2:95–113; see Sambrook et al., 1989, supra), or low (Chang and Cohen, 1978, J. Bacteriol. 134:1141–56; see also Miller, 1992, p. 10.4–10.11) copy number per cell depending upon the particular application.

For the selectable marker, preferably antibiotic resistance markers are used, such as the kanamycin resistance gene from Tn903 (Friedrich and Soriano, 1991, Genes Dev. 5:1513–1523), or genes that confer resistance to other aminoglycosides (including but not limited to dihydrostreptomycin, gentamycin, neomycin, paromycin and streptomycin), the TEM-1 β-lactamase gene from Tn9, which confers resistance to penicillin (including but not limited to ampicillin, carbenicillin, methicillin, penicillin N, penicillin O and penicillin V). Other selectable genes sequences including, but not limited to gene sequences encoding polypeptides which confer zeocin resistance (Hegedus et al. 1998, Gene 207:241–249). Other antibiotics that can be utilized are genes that confer resistance to amphenicols, such as chloramphenicol, for example, the coding sequence for chloramphenicol transacetylase (CAT) can be utilized (Eikmanns et al. 1991, Gene 102:93–98). As will be appreciated by one skilled in the art, other non-antibiotic methods to select for maintenance of the plasmid may also be used, such as, for example a variety of auxotrophic markers (see Sambrook et al., 1989, supra; Ausubel et al., supra).

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a TnpI fragment may be regulated by a second nucleic acid sequence so that the TnpI protein or peptide is expressed in a host transformed with the recombinant DNA molecule. For example, expression of TnpI coding sequence may be controlled by any promoter/enhancer element known in the art. Preferably the expression is controlled by an inducible promoter. Inducible expression yielding a wide range of expression can be obtained by utilizing a variety of inducible regulatory sequences. In one embodiment, for example, the lacI gene and its gratuitous inducer IPTG can be utilized to yield inducible, high levels of expression of TnpI when sequences encoding such polypeptides are transcribed via the lacOP regulatory sequences. A variety of other inducible promoter systems are well known to those of skill in the art which can also be utilized. Levels of expression from TnpI constructs can also be varied by using promoters of different strengths.

Other regulated expression systems that can be utilized include but are not limited to, the araC promoter which is inducible by arabinose (AraC) (see, e.g., Schleif, 2000, Trends Genet. 16:559–565), the TET system (Geissendorfer and Hillen, 1990, Appl. Microbiol. Biotechnol. 33:657–663), the $p_L$ promoter of phage λ temperature and the inducible lambda repressor $CI_{857}$ (Pirrotta, 1975, Nature 254: 114–117; Petrenko et al., 1989, Gene 78:85–91), the trp promoter and trp repressor system (Bennett et al., 1976, Proc. Natl. Acad. Sci USA 73:2351–55; Wame et al., 1986, Gene 46:103–112), the lacUV5 promoter (Gilbert and Maxam, 1973, Proc. Natl. Acad. Sci. USA 70:1559–63), lpp (Nokamura et al., 1982, J. Mol. Appl. Gen. 1:289–299), the T7 gene-10 promoter, phoA (alkaline phosphatase), recA (Horii et al., 1980, Proc. Natl. Acad. Sci. USA 77:313–7), and the tac promoter, a trp-lac fusion promoter, which is inducible by IPTG (Amann et al., 1983, Gene 25:167–78), for example, are all commonly used strong promoters, resulting in an accumulated level of about 1 to 10% of total cellular protein for a protein whose level is controlled by each promoter. If a stronger promoter is desired, the tac promoter is approximately tenfold stronger than lacUV5, but will result in high baseline levels of expression, and should be used only when overexpression is required. If a weaker promoter is required, other bacterial promoters are well known in the art, for example, maltose, galactose, or other desirable promoter (sequences of such promoters are available from GenBank (Burks et al. 1991, Nucl. Acids Res. 19:2227–2230).

For eukaryotic systems, vectors will include eukaryotic-specific promoter regions, which include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive or regulated. Promoters that may be used to control TnpI expression include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); plant expression vectors comprising the nopaline synthetase promoter region (Herrera-Estrella et al., 1984, Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, or the ADC (alcohol dehydrogenase) promoter.

Another option is to use a promoter that is tissue-specific, i.e., one whose expression is preferentially activated within a particular tissue and results in the expression of a gene product in the tissue where activated. Tissue-specific promoters that may be used include the PGK (phosphoglyceroyl kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes Dev. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al., 1987, Genes Dev. 1:161–171), beta-globin gene control region which is active in myeloid cells (Magram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the cloned DNA to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression (see, e.g., Kozak, 1991, J. Biol. Chem. 266:19867). Similarly, alternative codons, encoding the same amino acid, can be substituted for coding sequences in order to enhance translation (e.g., the codon preference of the host cell can be adopted, the presence of G-C rich domains can be reduced, and the like).

The vector may also contain nucleotide sequences of interest for protein expression, manipulation or maintenance of the inserted target DNA. For example, promoter sequences, enhancer sequences, translation sequences such as Shine and Dalgarno sequences, transcription factor recognition sites, Kozak consensus sequences, and termination signals may be included, in the appropriate position in the vector. For recombination cloning in cells other than bacterial cells, such as plant, insect, yeast or mammalian cells, other sequence elements may be necessary, such as species-specific origins of replication, transcription, processing, and translation signals. Such elements may include, but are not limited to eukaryotic origins of replication, enhancers, transcription factor recognition sites, CAT boxes, or Pribnow boxes.

Any method known in the art for delivering a DNA preparation comprising the target DNA into a host cell is suitable for use with the methods described above. Such methods are known in the art and include, but are not limited to electroporation of cells, preparing competent cells with calcium or rubidium chloride, and transduction of DNA with target DNA packaged in viral particles. For eukaryotic cells, methods include but are not limited to electroporation, transfection with calcium phosphate precipitation of DNA, and viral packaging. In a preferred embodiment, electroporation is used. Cells are treated to make them competent for electroporation by standard methods (see Ausubel et al., Current Protocols in Molecular Biology, Greene Publishing Associates and Wiley Interscience, New York). Preferably, about 50 μl of a standard preparation of electrocompetent cells is used for electroporation by standard procedures. In experiments that require the transformation of a linear or circular vector, 0.3 μg or more of vector is preferably used. In experiments that require the transformation of a DNA preparation containing the target DNA, 0.3 μg or more is preferably used. For co-transformation experiments, the DNAs are preferably mixed before electroporation. After electroporation, the cells are preferably diluted in culture medium and incubated for an approximately 1 and a half hours recovery period before culturing under conditions to identify the phenotypic change conveyed by the selectable marker gene.

Optimally, in prokaryotic cells, the phenotypic change is resistance to an antibiotic and the cells are cultured on plates that contain the corresponding antibiotic. In this case, the antibiotic resistant colonies that appear after overnight culture will predominantly contain the desired subcloning product.

In another embodiment, DNA is delivered into the host cell by transduction of DNA that has been packaged into a phage particle. P1 or λ transduction and packaging protocols are known in the art. Lambda packaging extracts are available commercially (e.g., from Promega, Madison, Wis.).

5.1.4 Cells Useful for TnpI-mediated Site-specific Recombination

Compositions include prokaryotic and eukaryotic cells containing DNA molecules comprising TRT or TRT' sequences. Where genetic manipulations of nucleotide sequences of interest by recombination is desirable, it is useful to have ready-made cells available that can express TnpI to achieve recombination events. In prokaryotic cells, this may be accomplished by the integration of an expression cassette, consisting of a TnpI coding sequence operably linked to a promoter, into the host cell in such a manner that TnpI production is effected. This may be accomplished, for example, by using homolgous recombination, transposon-mediated delivery systems, or λ integration to introduce the TnpI coding sequence into the host chromosome. Bacterial strains may also be engineered that carry a TnpI expression cassette on an episome or plasmid (see, e.g., Salamitou et al., 1997, Gene 202:121–26). Preferably, the promoter controlling TnpI expression is inducible.

The invention further relates to eukaryotic cells that contain at least one nucleotide sequence flanked by recombination targets, wherein the nucleotide sequence is excisable when TnpI contacts the recombination targets. The nucleotide sequence can be such that, upon TnpI-mediated recombination, the cell loses a gene function, gains a gene function, dies under certain conditions, or survives under certain conditions. The nucleotide sequence to be excised or inverted may be contained in an expression vector, a stable episome, or may be stably integrated into the genome of the host cell.

5.1.5 Kits

The invention also encompasses kits, comprising components useful for TnpI-mediated recombination packaged into suitable containers. Such kits include vectors suitable for the expression of TnpI in bacterial or eukaryotic cells, and may further include vectors suitable for the expression, and subsequent excision or inversion, of nucleotide sequences of interest, either by integration into the host genome or as episomes. Such kits may alternatively contain cells bearing DNA molecules with TnpI recombination target-flanked nucleotide sequences, as well as recombinant TnpI, or TnpI expression vectors for production of TnpI in vivo.

5.2 Methods for Use of TnpI-meditated Recombination

The methods described herein relate to the use of TnpI with the specific substrate sequences TRT and TRT' for TnpI-mediated recombination. Such recombination can be used to delete or insert DNA sequences, resulting in modulation of gene expression. The methods may be used in vivo or in vitro for engineering prokaryotic or eukaryotic genes.

Whereas recombination reactions with TRT substrates are fully reversible, recombination reactions utilizing TRT' are much less reversible. Thus, TRT sites may be used where reversibility of the reaction is desired. On the other hand, where greater stability is desired, stabilization of integration could be achieved using TRT (or a functional variant thereof) and transient expression of TnpI.

Generally, the methods described herein have the following common components: 1) a source of a functional TnpI protein, such as purified or recombinant TnpI recombinase or a cell or cell extract comprising TnpI activity; and 2) a substrate comprising TRT or TRT', or functional variants thereof, optionally flanking a target nucleotide sequence of interest.

5.2.1 In Vivo Methods

The invention encompasses in vivo methods for the use of the TnpI/TRT system for genetic engineering of prokaryotic or eukaryotic genes. In general, such methods utilize DNA replicons, such as, for example, DNA plasmid vectors or chromosomal DNA which are specifically designed to comprise TnpI recombination target sites, e.g., TRT or TRT' sequences, located at positions where recombination is desired to take place. Cells expressing TnpI activity, either constitutively or inducibly, are used as hosts for TnpI-mediated site-specific recombination. TnpI-mediated recombination may be used for deletion, insertion, or disruption of a gene of interest, or a particular domain of a gene of interest, or to make chromosomal alterations, such as large deletions and inversions, duplications and deletions by transallelic recombination, in inter- and intrachromosomal rearrangements (e.g., to alter antibody specificity or receptor specificity in particular cell types). Specific embodiments of these methods are described in detail hereinbelow.

5.2.1.1 Insertional Integration of DNA Sequences

In one aspect of the present invention, TnpI-mediated recombination may be used to integrate new nucleotide sequences into a DNA molecule, such as an episome or genomic DNA. Targeted integration of DNA sequences into a eukaryotic or prokaryotic genomes may be used, for example, for expression of heterologous gene sequences in transgenic animals and plants.

In one embodiment, for example, this may be accomplished by a two step process which involves the following steps. First, TnpI recombination target sites are introduced into the host genome, and second, a gene of interest is recombined into the genome at the TnpI recombination target sites via TnpI-mediated site-specific recombination. In a specific embodiment, insertion of one or more TnpI recombination target sites into the host genome may be accomplished by constructing an integration vector comprising two TnpI recombination target sites separated by a selectable marker. Preferably, the selectable marker is a negatively selectable marker, so that, in the second step, insertion of the gene sequence of interest can be selected by selecting against using the negatively selectable marker. Alternatively, naturally occurring TnpI recombination target sites, if they exist, may be used. In the next step, a gene sequence of interest, flanked by TnpI recombination target sites, is introduced into the host cell. TnpI is then expressed in the cell, allowing recombination at the TnpI recombination target sites, which results in insertion of the gene sequence of interest into the host genome between the TnpI recombination target sites.

5.2.1.2 Removal of DNA Sequences

Another aspect of the present invention is the use of TnpI as a site-specific recombinase to delete nucleotide sequences of interest, such as, e.g., selectable markers or other vector sequences, to disrupt gene function on an episome or in genomic DNA.

For example, in one embodiment, TnpI-mediated deletion reactions may be used for targeted excision of DNA sequences. In one embodiment, TnpI-mediated recombination may be used to delete a gene of interest from the genome of a higher organism. TnpI recombination target sites are inserted into the chomosome by homologous recombination flanking a gene of interest in direct repeat orientation. Expression of TnpI in such cells results in recombination at the TnpI recombination target sites and deletion of the gene of interest.

In a specific embodiment, the TnpI/TRT system may be used to create conditional knockout mutations in vivo, for example, in mice, in order to delete a desired gene sequence at a particular time or in a particular tissue. Such conditional knock-out mutations have been successfully produced using other site-specific recombinases, such as the Cre/lox system (for reviews, see Metzger and Feil, 1999, Current Opinion in Biotechnology, 10: 470–476; Sauer, 1998, Methods 14: 381–392). To this end, two directly repeated TnpI recombination target sites may be inserted into the genome by homologous and site-specific recombination in ES cells, such that the TnpI recombination target sites flank a gene of interest. Mice carrying such a "conditional" allele are crossed with TnpI-expressing transgenic mice. In the progeny, recombination will result in deletion of the gene of interest. Where the TnpI-expressing mice used are engineered to express TnpI in an inducible, developmental, or tissue specific manner, these methods may be used to induce spatio-temporally controlled genetic alterations in vivo. Thus, stabilization of integration may be achieved using TRT and transient expression of TnpI.

In another embodiment, TnpI-mediated recombination may be used to remove unnecessary sequences from a DNA molecule after a genetic engineering step. For example, when a heterologous nucleotide sequence is integrated into a genome or an episome, extraneous sequences are often co-integrated, such as vector sequences required for replication, maintenance, or selection of the integration vector. After insertion of the DNA sequence into the genome, such sequences are no longer necessary. Using the TnpI/TRT system of the present invention, such sequences may be removed. In a specific embodiment, for example, a mammalian cell line is transformed, preferably by electroporation, with a plasmid that contains a gene of interest and a selectable marker. The selectable marker is flanked by either TRT or, preferably, TRT' in the same orientation, creating a TRT'-selectable marker cassette that is operably separate from the gene of interest. Once stable integration is accomplished, the host cell line is transfected with a vector containing a TnpI-coding sequence operably linked to a promoter suitable for transient expression of the TnpI gene. Upon expression of TnpI, the selectable marker is excised from the genomic DNA, leaving the gene of interest intact.

These methods are useful, for example, for the purposes of gene therapy or any application aiming at producing food-grade genetically modified organisms (GMOs). In these applications it may be desirable to introduce into a genome a particular functionally-modifying gene, without the associated vector sequences that were required for maintenance of a vector in a bacterial host. Such sequences may re removed using the TnpI-mediated deletion reaction described herein. In another embodiment, marker sequences used for selection of recombinants may be removed. Specifically, a vector comprising: 1) a eukaryotic gene of interest, 2) a bacterial selectable marker, and 3) origin of replication is used to transform plant cells, by homologous recombination of the gene into the cellular DNA. For genetically-modified plants, the eukaryotic gene is desirable, but the origin of replication and selectable marker, which in the field may be transferred horizontally to sensitive bacteria, are particularly undesirable. To remove these unwanted sequences after introducing the gene of interest, a plasmid vector is constructed comprising: (1) a gene segment to be integrated into the plant cells' genomic DNA; (2) a bacterial host-relevant selectable marker, and (3) two TnpI recombination target sites that flank the selectable marker and origin of replication in such a manner that, when recognized by TnpI, the bacterial-relevant genes are excised. The vector is linearized and transformed into the new host cells. Once integration and expression of the desired gene has occurred, the bacterial-relevant marker and origin can be removed by TnpI-mediated recombination, as described above.

TnpI-mediated recombination in vivo can also be used to disrupt gene function. This can be accomplished by inserting one or more TnpI recombination target sites in or adjacent to an endogenous gene of interest, whose function is desired to be disrupted. TnpI is then expressed in the cell, resulting in recombination between the TnpI recombination target sites, a concomitant loss of gene function. Preferably, TnpI is expressed by induction of TnpI residing on a plasmid under the control of an inducible promoter. Preferably, the plasmid contains an appropriate origin of replication conferring medium copy number to high copy number, and a gene that confers resistance to an antibiotic to which the host is sensitive.

In a specific embodiment, for example, a prokaryotic host capable of expressing TnpI as above is used. The second plasmid contains, in order, a selectable marker, a recombination target, a second selectable marker oriented so as to be transcribed in a direction opposite to that of the first selectable marker, a second recombination target, and a promoter in the same orientation as the first selectable marker and capable of driving expression of the first selectable marker upon recombination. Preferably the selectable markers confer antibiotic resistance, but may also confer prototrophy to the appropriate auxotrophic strain. Prior to recombination, only the second selectable marker is expressed. Upon expression of TnpI, however, the second selectable marker is excised and lost; the excision joins the promoter and first selectable marker, which is then expressed.

5.2.1.3 Induction of Gene Expression

In another aspect of the invention, TnpI-mediated site specific recombination may be used to modulate, i.e., increase or decrease, the expression of specific genes within a host cell. In one embodiment, a vector is constructed comprising a promoter, a gene of interest, and a spacer sequence separating the promoter and the gene of interest such that the promoter is not operably associated with the gene and no expression occurs. The spacer sequence is flanked by two directly repeated TnpI recombination target sites. When TnpI is expressed in the cell, recombination between the target sites results in excision of the spacer. This results in the promoter becoming operably associated with the gene of interest, inducing in gene expression. If desired, the spacer region may comprise a selectable marker, preferably a negative selectable marker, so that removal of the spacer region may be selected for. In this embodiment, TnpI expression can be accomplished in a number of different ways, including introducing an expression vector that expresses TnpI, in an inducible or constitutive manner. For example, to induce TnpI expression, a second vector comprising a TnpI coding sequence operably linked to an inducible or constitutive promoter may be introduced into the host cell.

In another embodiment, TnpI-mediated recombination is used to control the expression of a target gene by regulating the expression of a regulatory molecule, such as, for example, a transcription factor which induces expression of a gene, or an inhibitory factor to repress the expression of the gene. A vector containing the DNA sequence of the regulatory molecule flanked by recombination sites is introduced into a eukaryotic cell. A second DNA sequence comprising an inducible TnpI gene is also introduced into the cell. Upon activation of the TnpI gene, the gene for the regulatory molecule is deleted, and the target gene becomes activated or inactivated.

In another embodiment, the TnpI/TRT system may be used to for in vivo expression technology to identify transient expression of genes in eukaryotic and Gram-negative bacterial cells in response to particular growth conditions or other environmental signals. This method is described by Salimitou et al. (Salamitou et al., 1997, supra), but is limited to use in Gram-positive bacteria. In this method, two compatible plasmids are constructed, a TnpI expression plasmid and a reporter plasmid. The expression plasmid is constructed with a promoterless TnpI gene, into which gene sequences, e.g. sequences derived from a genomic library, may be inserted. Activation of a promoter cloned upstream from the promoterless TnpI gene results in expression of TnpI, which, in turn, mediates recombination between the two TnpI recombination target sites, leading to excision of the selectable marker. A second plasmid, the reporter plasmid, which is compatible with the first plasmid, comprises one or more selectable marker sequences and two directly repeated TnpI recombination target sites. The reporter plasmid may be set up to accommodate either positive or negative selection system, or both. Where a negative selection is desired, the reporter plasmid is engineered so that TnpI recombination target sites flank the negatively selectable marker in direct repeat orientation, such that TnpI expression leads to excision of the marker. Thus, recombinant cells can be selected for by selecting against the negatively selectable marker. Alternatively, or in addition to the negatively selectable marker, a positive selection system may be used. In this case, the reporter plasmid is engineered so that excision of the sequences between the TnpI recombination target sites results in the generation of a functional positive selectable marker. In this method, the TnpI recombination target site is preferably TRT', which favors the intramolecular excision reaction. This system may be used to screen eukaryotic and prokaryotic genomic libraries for nucleotide sequences which respond to environmental signals, allowing the identification of genes involved in important signaling pathways.

5.2.2 In Vitro Methods

The invention also encompasses in vitro methods for genetic engineering of prokaryotic or eukaryotic genes. In these methods, a purified or isolated TnpI activity is supplied to a substrate DNA molecule comprising TRT or TRT' sites. Preferably, purified recombinant TnpI is used. The substrate DNA molecule used in these in vitro methods comprises a DNA molecule containing two directly repeated TRT or TRT' sites, between which sites resides a target nucleotide sequence whose rearrangement is desired, i.e., the target sequence to be deleted or inserted into a second substrate molecule. The substrate is preferably a supercoiled DNA molecule.

In one embodiment, for example, in vitro TnpI recombination reactions are performed as follows. A supercoiled DNA plasmids containing two copies a functional TnpI recombination target site sequence is used as a recombination substrate. Recombination reactions are performed in 20 µl volume using approximately 500 ng of TnpI recombinase protein and DNA substrate in a buffer containing 50 mM Tris-HCl pH 8.0, 25 mM KCL, 1.25 mM EDTA, 5 mM spermidine, 10% glycerol and 25 µg/Ml BSA, and incubated at 37° C. for different times. In a preferred embodiment the incubation time is 30 minutes. Preferably, the TnpI recombinase protein is purified. The recombination products may be analysed by restriction enzyme digestion followed by agarose gel electrophoresis of the reactions.

In various embodiments, for example, the in vitro TnpI recombination reaction is used for the construction and manipulation of recombinant DNA molecules in vitro. Such methods have been described for use with other site-specific recombinases, such as the Cre/lox system (see U.S. Pat. No. 5,851,808, issued Dec. 22, 1998; International Publication No. WO 00/05355, published Feb. 3, 2000; Liu et al., 2000, Methods in Enzymology 328: p 530–549). Using the TnpI/TRT system in vitro, one can rearrange, shuffle, and subclone DNA molecules from one type of vector into another, without the need for costly restriction enzymes, ligases and time-consuming and labor intensive in vitro manipulations. For example, in one embodiment, the TpnI/TRT system may be used to subclone or "shuttle" a nucleotide sequence (or library of nucleotide sequences) of interest from a first DNA molecule (a "donor" vector) into a second DNA molecule (a "recipient" vector), which recipient vector is particularly suited for a desired purpose, such as expression in a particular host cell type. The donor vector comprises a TnpI recombination target site, the gene of interest, an origin of replication, and, optionally, one or more selectable marker genes. The recipient molecule comprises one or more nucleotide regulatory sequences juxtaposed to a TnpI recombination target, an origin of replication, and, optionally, one or more selectable marker genes. The nucleotide regulatory sequence may be any sequence that may modify, promote or enhance expression of the gene interest in the host cell. Examples of such nucleotide regulatory sequences include, but are not limited to, eukaryotic or prokaryotic transcriptional regulatory sequences such as promoters, enhancer elements, and/or transcription factor binding sites, such as cell-type specific or tissue-specific transcription factor binding sites, translational regulatory elements, and/or post-translational processing sites. Preferably, in this embodiment, where unconstrained recombination activity is desirable, the TnpI recombination target site is a TRT sequence.

In another embodiment, for example, the in vitro deletion reaction between TnpI recombination target sites may be used to produce circular DNA molecules devoid of undesired nucleotide elements. Such a method may be used, for example, in the construction of DNA vaccines, where it would be desirable to remove unnecessary vector sequences from a DNA molecule before administration of the DNA vaccine to a subject. For example, such a vector may be constructed by placing the DNA sequence of interest between two directly repeated TnpI recombination target sites, which are later useful for removing the replication origin and resistance marker genes, producing a final DNA vaccine product useful for therapeutic treatment. Preferably, in this embodiment, where the constrained recombination activity may be desirable, the TnpI recombination target is a TRT' sequence.

Finally, the TnpI/TRT system may be used in conjunction with other site specific recombination systems with different specificities, e.g., Cre/lox or Flp/FRT recombinases, to expand the versatility of the in vitro methods (Meyers et al., 1998, Nat. Genet. 18:136–41). For example, plasmid vectors comprising both TnpI recombination target sites together with one or more other site-specific recombinase recognition sites could be used to delete, insert, and/or rearrange DNA sequences at particular steps of a multi-step cloning process. Such methods may be particular useful, for example, in the fields of proteomics and directed evolution to construct novel proteins with novel activities which require for multi-step shuffling methods.

6. EXAMPLES

The invention is illustrated by the following experiments, which analyze the site-specific recombinase activity of TnpI both in vivo and in vitro.

The examples presented hereinbelow demonstrate that TnpI mediates recombination, both in vivo and in vitro, using two distinct target sites, the minimal TRT site and the full TRT' site, and that TnpI activity at these two distinct sites leads to topologically distinct intermediates and functionally distinct recombinant products. The experiments further demonstrate that TnpI is active in a broad range of host cells, without the need for accessory factors. As demonstrated herein, these previously unknown abilities of TnpI and its recombination substrates have important implications for the use of TnpI recombinase in genetic engineering.

6.1 Analysis of TnpI-mediated Recombination In Vivo

One of the limitations of use of other well known recombinases, such as Cre/lox or Flp/FRT, is the complete reversibility of their reaction mechanisms. Consequently, the rate of production of final product is impeded by the rate at which product undergoes the reverse reaction to reform the substrate (Logie and Stewart, 1995, Proc. Natl. Acad. Sci. USA 92: 5940–5944). The experiments in this section demonstrate that the reversibility of TnpI-mediated site-specific recombination depends on the nature and structure of the recombination target site. Thus, substrates can be specifically designed according to the desired reversibility of the excision/insertion reaction.

6.1.1 Differential Activities of TRT' and TRT Substrate S

Previous reports identified a 249 bp fragment of transposon Tn4430 as the shortest DNA fragment that includes the sequences required for TnpI recombination (See FIG. 2; Salamitou et al., 1997, supra; Sanchis et al., 1997, supra). As depicted in FIG. 2, this region contains three distinct TnpI binding sites: a 32 bp inverted repeat sequence, and two downstream 16 bp direct repeat sequences. To analyze the requirements for TnpI-mediated recombination, Tnp1-mediated recombination was analyzed in the heterologous host *E. coli*.

For heterologous expression, an inducible TnpI expression vector, pYZ-BAD-TnpI, was constructed. pYZ-BAD-TnpI was created by inserting the coding sequence for TnpI, shown in FIG. 3, into the vector pBAD24, such that the expression of TnpI was under the control of the arabinose-inducible promoter, $P_{BAD}$. The resultant vector, pYZ-BAD-TnpI, as shown in FIG. 4, comprises $P_{BAD}$ operatively linked to the TnpI coding sequence, a p15A replication origin, a kanamycin resistance selectable marker, and AraC, the arabinose-responsive repressor that regulates $P_{BAD}$. (In addition, pBAD expression vectors have been constructed which express TnpI as a His-tag fusion protein. Both forms of protein were found to be equally active, both in vivo and in vitro.)

Initially, Tnp1-mediated recombination was tested in *E. coli* using a "full-length" TnpI recombination target sequence. Two copies of a 244 bp fragment comprising the left IR and all four TnpI binding sites, called TRT" (see FIG. 1A), were cloned into a plasmid in direct repeat orientation and used as a substrate for recombination in *E. coli*. This plasmid construct was then transformed into *E. coli* cells containing the TnpI expression plasmid pYZ-BAD-TnpI, and induced with arabinose. Using TRT", recombination was detected upon induction of TnpI, indicating that the heterologous host *E. coli* supports TnpI-mediated recombination.

To further refine the sequence requirements of TnpI-mediated recombination, various substrates were tested for recombination activity in *E. coli* cells expressing TnpI. DNA plasmids containing directly repeated copies of TnpI recombination target sites of various lengths were tested as substrates. In particular, plasmids were constructed containing directly repeated copies of either the abbreviated 116 bp TnpI recombination target site, TRT' (shown in FIG. 1B), containing both the 32 bp inverted repeat sequence and the two downstream 16 bp direct repeat sequences, or the shorter 32 bp TnpI recombination target site, TRT (shown in FIG. 1C), containing only the 32 bp inverted repeat sequences. Plasmids containing TRT or TRT' sites were introduced into *E. coli* cells in the presence or absence of a TnpI expression plasmid. Plasmid products were then purified from the cells and separated on agarose gels containing ethidium bromide.

The result is shown in FIGS. 5A–B. As depicted in FIG. 5A, complete recombination between a substrate, S, containing the two recombination sites produces two recombination products, P, one of which lacks a plasmid origin (indicated by a filled circle) and is therefore unable to replicate in vivo. Products of TnpI-mediated recombination in *E. coli* are shown in the agarose gel depicted in FIG. 5B. Plasmids containing TRT or TRT' sites were tested in the presence of TnpI expression. The results of this experiment indicate that DNA plasmids containing directly repeated 116 bp TRT' sites yielded the expected recombination product in the presence of TnpI expression (lane 5), but not in the absence of TnpI expression (lane 4). However, using the DNA plasmid comprising the minimal TRT (lanes 6 and 7), an unexpected result was obtained. Rather than the lower-molecular weight band representing the expected product, a ladder of multiple higher-molecular weight bands was observed upon induction of TnpI expression (lane 7). This ladder of high molecular weight bands represents a series of plasmid multimers, the products of intermolecular recombination, rather than deletion. A small amount of the expected lower molecular weight product is observed seen at the bottom of the ladder.

These unexpected results indicate that the 116 bp TRT and the shorter 32 bp TRT exhibit functionally distinct properties as TnpI recombination substrates. Apparently, when TRT' is used a substrate, the intramolecular (forward) reaction, which yields the two products, is topologically different from the intermolecular (backward) reaction, which recreates the starting material DNA substrate. This may be explained by a difference in the topological states of the TnpI-TRT complex versus TnpI-TRT' protein complexes. The TRT' complex may provide an asymmetric component so that the intermolecular reaction is favored over the intramolecular reaction. This topological component is discussed further below (see Section 6.2.3 and FIG. 9 below).

In sum, the use of alternative, distinct TnpI recombination target sites allows options for use in genetic engineering. Thus, the use of the full TRT' favors the forward, intramolecular excision reaction, and disfavors the reverse, intermolecular insertion reaction. On the other hand, the use of the full length TRT' can be used when the irreversible intramolecular excision reaction is desired.

6.2 Analysis of TnpI-mediated Recombination In Vitro

The following in vitro recombination experiments were performed to identify the functional domains and in vitro requirements of TnpI-mediated recombination. Importantly, it was found that the purified TnpI is sufficient to promote recombination at the TRT and TRT' sites, albeit with different efficiencies, and that additional auxiliary factors are not required. Topological analysis of the in vitro recombination products also revealed that recombination at TRT and TRT' involves the formation of recombination complexes with different level of complexity.

6.2.1 TnpI Overexpression and Purification

To overexpress the TnpI protein in *E. coli*, a BglII-HindIII DNA fragment carrying the TnpI coding sequence was amplified by PCR and inserted into the pBAD/HisA expression vector (Invitrogen). As depicted in FIG. 6A (upper panel), the resulting plasmid, pGIV007, encodes a His-tag::TnpI fusion protein, H-TnpI, the expression of which is under the control of the *E. coli* arabinose operon promoter, pBAD. An NcoI deletion of pGIV007 was constructed in order to delete the His-tag region and to generate the plasmid pGIV008, which expresses the wild-type TnpI protein (FIG. 6A, lower panel). Cultures of *E. coli* cells containing these two plasmids were induced with 0.2% L-arabinose, and the expressed proteins were purified (H-TnpI) or partially purified (TnpI) by affinity chromatography on nickel resin, and displayed by SDS PAGE gel electrophoresis as shown in FIG. 6B.

6.2.2 Differential Activity of TRT' AND TRT In Vitro

The recombination activity of TnpI and H-TnpI was examined in vitro. DNA plasmids containing either two directly repeated copies of the TRT site (pGIV016) or two directly repeated copies of the TRT' site (pGIV014) were used as recombination substrates. As depicted schematically in FIG. 7A, complete recombination between the two TRT or TRT' copies results a deletion reaction, producing two smaller plasmids, each with a single TnpI recombination target site. Recombination reactions were performed with ~500 ng of purified recombinase protein and supercoiled DNA in a volume of 20 µl, containing 50 mM Tris-HCl pH 8.0, 25 mM KCL, 1.25 mM EDTA, 5 mM spermidine, 10% glycerol and 25 µg/Ml BSA. Reactions were incubated at 37° C. for 30 min.

The recombination reactions were then analyzed by the restriction enzyme digestion, followed by electrophoresis in a 0.8% agarose after digestion with HindIII. Since the starting plasmids each contained two HindIII sites, digestion with HindIII yields two fragments, S1 and S2 (see FIG. 7A). However, HindIII digestion of the recombination products, each of which contains a single HindIII site, yields two distinguishable fragments, P1 and P2 (see FIG. 7A). Thus, HindIII digestion readily distinguished the starting material from the two products. As shown in the agarose gels in FIG. 7B, HindIII digestion of the recombination reactions resulted in the expected size fragments corresponding to starting material and recombination products using both TRT and TRT' as substrates. Thus, these results demonstrated that the purified TnpI protein is sufficient to promote efficient recombination at TRT and TRT' in vitro, without requiring additional host factors.

Next, a kinetic time-course analysis of TnpI-mediated recombination in vitro reactions was performed using TRT and TRT'. FIG. 7C shows the results of a time course analysis of recombination at TRT (squares) and TRT' (diamonds). For each time point, the proportion of the products was quantified by densitometry analysis of an electrophoresis gel containing HindIII-digested reactions. This analysis revealed that recombination of a plasmid carrying two directly repeated TRT' sequences is faster than recombination of a similar plasmid containing the TRT core sequence, indicating that the additional TnpI binding sites in TRT' stimulated recombination. Similar recombination activity was observed for the wild-type and His-tagged TnpI proteins, demonstrating that the recombinase tolerates N-terminal peptide fusions.

6.2.3 Recombination at TRT and TRT' Involves the Formation of Recombination Complexes with Different Levels of Complexity The topology of in vitro recombination products was analyzed by treating the reactions with DNase I in the presence of ethidium bromide. This treatment introduces single nicks in DNA, allowing removal of supercoiling while perserving the intercatenation nodes introduced into the substrate during recombination (see FIG. 8A). Plasmid substrates were incubated in the presence or absence of H-TnpI, and then treated in reactions with 1 µg/ml of DNase I (+) and 0.3 mg/ml of ethidium bromide, or without DNase I (−), as indicated. Nicked reactions were then analyzed by high resolution agarose gel electrophoresis (0.7% agarose) to compare the complexity of the products resulting from TRT or TRT' recombination.

As shown in FIG. 8A, intramolecular recombination between directly repeated TRT sequences generated a variety of deletion products (catenanes) in which the two DNA circles remained interlinked a certain number (i.e., 2, 4, 6, etc.; labeled 2, 4, and 6 in FIG. 8A) of times. Recombination also produced faint bands corresponding to knotted DNA molecules containing 3, 5, etc. nodes (labeled 3 and 5 in FIG. 8A). Such knots arose from consecutive recombination events using the initial catenated products as a substrate. These results indicate that TRT recombination occurs freely by random collision between recombination sites.

In contrast, the TRT' recombination substrate yielded exclusively 2-noded catenane products (FIG. 8B). This result indicated that recombination is catalyzed within a protein-DNA complex having a specific geometry. Assembly of the recombination complex may involve multiple interactions between TnpI molecules bound onto the inverted and direct repeats of TRT'. According to the current model, depicted in FIG. 9, the topology of the DNA within this complex is such that it can only form efficiently if the two recombination sites are present in tandem on a same DNA molecule, thereby providing directionality to the recombination reaction. When TnpI is also bound to the direct repeats (DR1, DR2), a specific higher order wrapping is created in addition to the one formed when TnpI is bound to TRT.

6.3 TnpI-mediated Recombination in Eukaryotic Cells

The experiments in this section demonstrate the ability of TnpI to mediate site-specific recombination in eukaryotic cells. A eukaryotic TnpI recombination reporter cell line was constructed by introducing pSVpaT, depicted in FIG. 10, into mouse ES cells. As shown in FIG. 10, pSVpaT contains an SV40 promoter, a puromycin resistance gene flanked by two direct copies of a 32 bp TRT sequence containing the inverted repeat, the β-galactosidase gene (lacZ), and the chloramphenicol resistance gene.

The nucleotide sequence encoding TnpI was cloned into the eukaryotic expression plasmid pCAGGS to construct the eukaryotic TnpI expression plasmid pCAGGS/TnpI, which is depicted in FIG. 11. pCAGGS includes the TnpI coding sequence, the expression of which is driven by the chicken beta-actin promoter $P_{CBA}$.

ES cells containing stably integrated pSVpaT sequences were selected for by selecting for puromycin resistance. Before TnpI-mediated recombination, these TnpI reporter ES cells do not express LacZ (see FIG. 12, top). However, TnpI-mediated recombination removes the puromycin resistance gene, which lies between the SV40 promoter and lacZ, and juxtaposes the lacZ gene next to the SV40 promoter (see FIG. 12, bottom). Thus, recombination results in the expression of lacZ, which can be detected by the appearance of blue colonies upon the introduction of lactose.

FIG. 13 shows the results of this experiment. Introduction of the pCAGGS/TnpI expression vector into the TnpI reporter ES cells resulted in the expression of LacZ, as indicated by the presence of blue colonies, shown in FIG. 13.

This previously unreported ability of TnpI to catalyze site-specific recombination in eukaryotic hosts expands the commercial potential of TnpI for genetic engineering.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, including patent applications and publications, the contents of each of which is hereby incorporated by reference into the present application in its entirety for all purposes.

What is claimed is:

1. A composition comprising an isolated DNA molecule comprising TRT (SEQ ID NO:3), or SEQ ID NO:3 that is altered in the central crossover region, with the proviso that the DNA molecule does not comprise the entire sequence of TRT" (SEQ ID NO:4).

2. The composition of claim 1 wherein the DNA molecule further comprises a heterologous nucleotide sequence.

3. The composition of claim 1 wherein the DNA molecule does not comprise more than 200 contiguous nucleotides of the sequence TRT" (SEQ ID NO:4).

4. The composition of claim 3 wherein the DNA molecule does not comprise more than 100 contiguous nucleotides of TRT" (SEQ ID NO:4).

5. The composition of claim 3 wherein the DNA molecule does not comprise more than 32 contiguous nucleotides of TRT" (SEQ ID NO:4).

6. The composition of any one of claims 1 to 5 wherein the DNA molecule further comprises a selectable marker.

7. The composition of any one of claims 1 to 5 wherein the DNA molecule is a vector.

8. A cell transformed with a DNA molecule, said DNA molecule comprising TRT (SEQ ID NO:3) or SEQ ID NO:3 that is altered in the central crossover region, with the proviso that the DNA molecule does not comprise the entire sequence of TRT" (SEQ ID NO:4).

9. The cell of claim 8 wherein the DNA molecule is integrated into the chromosome of the cell.

10. A eukaryotic cell transformed with a DNA molecule integrated into its chromosome, said DNA molecule comprising TRT (SEQ ID NO:3) or SEQ ID NO:3 that is altered in the central crossover region.

11. The cell of claim 10, which is a mouse embryonic stem cell.

12. The cell of claim 10 wherein the DNA molecule comprises two copies of TRT (SEQ ID NO:3) or SEQ ID NO:3 that is altered in the central crossover region, separated by a heterologous nucleotide sequence.

13. The eukaryotic cell of claim 10, wherein the DNA molecule comprises SEQ ID NO:3 that is altered in the central crossover region.

14. The eukaryotic cell of claim 10, wherein the DNA molecule comprises TRT' (SEQ ID NO:2) or SEQ ID NO:2 that is altered in the central crossover region.

15. The eukaryotic cell of claim 10, wherein the DNA molecule comprises SEQ ID NO:2 that is altered in the central crossover region.

16. The cell of claim 14 wherein the DNA molecule comprises two copies of TRT' (SEQ ID NO:2) or SEQ ID NO:2 that is altered in the central crossover region, separated by a heterologous nucleotide sequence.

17. A kit comprising in separate containers:
   a) an isolated DNA molecule comprising one or more copies of TRT (SEQ ID NO:3) or SEQ ID NO:3 that is altered in the central crossover region; and
   b) an isolated TnpI protein, a TnpI expression vector or a cell capable of expressing TnpI,
   with the proviso that the DNA molecule does not comprise the entire sequence of TRT" (SEQ ID NO:4).

18. The kit of claim 17, wherein the DNA molecule comprises SEQ ID NO:3 that is altered in the central crossover region.

19. The composition of claim 1, wherein the isolated DNA molecule comprises TRT (SEQ ID NO:3).

20. The composition of claim 1, wherein the isolated DNA molecule comprises a sequence selected from the group consisting of SEQ ID NO:7, SEQ ID NO:8, SEQ ID NO:9, and SEQ ID NO:10.

21. The composition of claim 1, wherein the isolated DNA molecule comprises TRT' (SEQ ID NO:2).

22. The composition of claim 1, wherein the isolated DNA molecule comprises at least two copies of TRT (SEQ ID NO:3).

23. The composition of claim 1, wherein the isolated DNA molecule comprises at least two copies of TRT' (SEQ ID NO:2).

24. The cell of claim 8, wherein the DNA molecule comprises TRT (SEQ ID NO:3).

25. The cell of claim 8, wherein the DNA molecule comprises a sequence selected from the group consisting of SEQ ID NO:7, SEQ ID NO:8, SEQ ID NO:9, and SEQ ID NO:10.

26. The cell of claim 8, wherein the DNA molecule comprises TRT' (SEQ ID NO:2).

27. The cell of claim 8, wherein the DNA molecule comprises at least two copies of TRT (SEQ ID NO:3).

28. The cell of claim 8, wherein the DNA molecule comprises at least two copies of TRT' (SEQ ID NO:2).

29. The kit of claim 17, wherein the isolated DNA molecule comprises TRT (SEQ ID NO:3).

30. A kit comprising in separate containers:
a) an isolated DNA molecule comprising one or more copies of TRT (SEQ ID NO:3) or SEQ ID NO:3 that is altered in the central crossover region; and
b) an isolated TnpI protein, a TnpI expression vector or a cell capable of expressing TnpI,
wherein the isolated DNA molecule comprises a sequence selected from the group consisting of SEQ ID NO:7, SEQ ID NO:8, SEQ ID NO:9, and SEQ ID NO:10.

31. The kit of claim 17, wherein the isolated DNA molecule comprises TRT' (SEQ ID NO:2).

32. A kit comprising in separate containers:
a) an isolated DNA molecule comprising one or more copies of TRT (SEQ ID NO:3) or SEQ ID NO:3 that is altered in the central crossover region; and
b) an isolated TnpI protein, a TnpI expression vector or a cell capable of expressing TnpI,
wherein the isolated DNA molecule comprises at least two copies of TRT (SEQ ID NO:3).

33. A kit comprising in separate containers:
a) an isolated DNA molecule comprising one or more copies of TRT (SEQ ID NO:3) or SEQ ID NO:3 that is altered in the central crossover region; and
b) an isolated TnpI protein, a TnpI expression vector or a cell capable of expressing TnpI,
wherein the isolated DNA molecule comprises at least two copies of TRT' (SEQ ID NO:2).

34. The composition of claim 1, wherein the isolated DNA molecule comprises SEQ ID NO:3 that is altered in the central crossover region.

35. The cell of claim 8, wherein the DNA molecule comprises SEQ ID NO:3 that is altered in the central crossover region.

* * * * *